US008632547B2

(12) United States Patent
Maxson et al.

(10) Patent No.: US 8,632,547 B2
(45) Date of Patent: Jan. 21, 2014

(54) PATIENT-SPECIFIC OSTEOTOMY DEVICES AND METHODS

(75) Inventors: William Maxson, Fort Wayne, IN (US); Kevin T. Stone, Winona Lake, IN (US); Andrew L. Pierce, Warsaw, IN (US); Robert Metzger, Wakarusa, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 92 days.

(21) Appl. No.: 13/106,295

(22) Filed: May 12, 2011

(65) Prior Publication Data

US 2011/0213376 A1 Sep. 1, 2011

Related U.S. Application Data

(63) Continuation-in-part of application No. 12/714,023, filed on Feb. 26, 2010, now Pat. No. 8,241,293.

(51) Int. Cl.
*A61B 17/58* (2006.01)

(52) U.S. Cl.
USPC .......................................................... 606/88

(58) Field of Classification Search
CPC .................................................. A61B 17/1604
USPC ........... 606/84–88, 79, 89, 80, 82; 623/20.32, 623/18.11, 20.16, 20.17
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A * | 12/1983 | Mains et al. ................... 606/88 |
| 4,436,684 A | 3/1984 | White |
| 4,475,549 A | 10/1984 | Oh |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

Biomet "Oxford® Partial Knee" brochure, 8 pages (Feb. 2011).

(Continued)

*Primary Examiner* — Alvin J. Stewart
(74) *Attorney, Agent, or Firm* — Harness, Dickey

(57) ABSTRACT

An osteotomy method includes attaching a patient-specific osteotomy guide to a corresponding surface of a tibia of a patient and making an osteotomy at a patient-specific orientation through a resection slot of the osteotomy guide. The osteotomy guide is removed and first and second faces of the osteotomy are opened to form an implant insertion angle. The first and second faces of the osteotomy are secured at the implant insertion angle and an osteotomy implant having a patient-specific wedge angle that is smaller than the implant insertion angle is implanted. The first and second faces of the osteotomy are brought to the patient-specific wedge angle and in contact with the osteotomy implant.

14 Claims, 21 Drawing Sheets

(56) References Cited

U.S. PATENT DOCUMENTS

| | | | |
|---|---|---|---|
| 4,506,393 A | 3/1985 | Murphy |
| 4,524,766 A | 6/1985 | Petersen |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,719,907 A | 1/1988 | Banko et al. |
| 4,721,104 A | 1/1988 | Kaufman et al. |
| 4,722,330 A | 2/1988 | Russell et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,030,221 A | 7/1991 | Buechel et al. |
| 5,041,117 A | 8/1991 | Engelhardt |
| 5,053,037 A | 10/1991 | Lackey |
| 5,053,039 A * | 10/1991 | Hofmann et al. ........... 606/87 |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,246,444 A | 9/1993 | Schreiber |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,364,402 A * | 11/1994 | Mumme et al. ........... 606/88 |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,417,694 A * | 5/1995 | Marik et al. ........... 606/88 |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A * | 3/1997 | Jenkins, Jr. ........... 606/87 |
| 5,620,448 A * | 4/1997 | Puddu ........... 606/87 |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A * | 3/1998 | Jenkins, Jr. ........... 606/87 |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A * | 7/1999 | Legrand ........... 606/87 |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A * | 7/2000 | Bonutti ........... 606/87 |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |

(56) References Cited

U.S. PATENT DOCUMENTS

| | | | |
|---|---|---|---|
| 6,312,258 B1 | 11/2001 | Ashman | |
| 6,312,473 B1 | 11/2001 | Oshida | |
| 6,319,285 B1 | 11/2001 | Chamier et al. | |
| 6,325,829 B1 | 12/2001 | Schmotzer | |
| 6,343,987 B2 | 2/2002 | Hayama et al. | |
| 6,354,011 B1 | 3/2002 | Albrecht | |
| 6,379,299 B1 | 4/2002 | Borodulin et al. | |
| 6,383,228 B1 | 5/2002 | Schmotzer | |
| 6,391,251 B1 | 5/2002 | Keicher et al. | |
| 6,395,005 B1 | 5/2002 | Lovell | |
| 6,427,698 B1 | 8/2002 | Yoon | |
| 6,459,948 B1 | 10/2002 | Ateshian et al. | |
| 6,463,351 B1 | 10/2002 | Clynch | |
| 6,475,243 B1 | 11/2002 | Sheldon et al. | |
| 6,482,236 B2 | 11/2002 | Habecker | |
| 6,488,715 B1 | 12/2002 | Pope et al. | |
| 6,503,255 B1 | 1/2003 | Albrektsson et al. | |
| 6,510,334 B1 | 1/2003 | Schuster et al. | |
| 6,514,259 B2* | 2/2003 | Picard et al. | 606/88 |
| 6,517,583 B1 | 2/2003 | Pope et al. | |
| 6,520,964 B2 | 2/2003 | Tallarida et al. | |
| 6,533,737 B1 | 3/2003 | Brosseau et al. | |
| 6,547,823 B2 | 4/2003 | Scarborough et al. | |
| 6,554,837 B1 | 4/2003 | Hauri et al. | |
| 6,556,008 B2 | 4/2003 | Thesen | |
| 6,558,391 B2 | 5/2003 | Axelson, Jr. et al. | |
| 6,558,428 B2 | 5/2003 | Park | |
| 6,564,085 B2 | 5/2003 | Meaney et al. | |
| 6,567,681 B1 | 5/2003 | Lindequist | |
| 6,575,980 B1 | 6/2003 | Robie et al. | |
| 6,575,982 B1 | 6/2003 | Bonutti | |
| 6,591,581 B2 | 7/2003 | Schmieding | |
| 6,605,293 B1 | 8/2003 | Giordano et al. | |
| 6,622,567 B1 | 9/2003 | Hamel et al. | |
| 6,629,999 B1 | 10/2003 | Serafin, Jr. | |
| 6,641,617 B1 | 11/2003 | Merrill et al. | |
| 6,682,566 B2 | 1/2004 | Draenert | |
| 6,696,073 B2 | 2/2004 | Boyce et al. | |
| 6,697,664 B2 | 2/2004 | Kienzle, III et al. | |
| 6,701,174 B1 | 3/2004 | Krause et al. | |
| 6,709,462 B2 | 3/2004 | Hanssen | |
| 6,711,431 B2 | 3/2004 | Sarin et al. | |
| 6,711,432 B1 | 3/2004 | Krause et al. | |
| 6,712,856 B1 | 3/2004 | Carignan et al. | |
| 6,716,249 B2 | 4/2004 | Hyde | |
| 6,725,077 B1 | 4/2004 | Balloni et al. | |
| 6,738,657 B1 | 5/2004 | Franklin et al. | |
| 6,740,092 B2 | 5/2004 | Lombardo et al. | |
| 6,749,638 B1 | 6/2004 | Saladino | |
| 6,750,653 B1 | 6/2004 | Zou et al. | |
| 6,772,026 B2 | 8/2004 | Bradbury et al. | |
| 6,780,190 B2 | 8/2004 | Maroney | |
| 6,786,930 B2 | 9/2004 | Biscup | |
| 6,799,066 B2 | 9/2004 | Steines et al. | |
| 6,823,871 B2* | 11/2004 | Schmieding | 128/898 |
| 6,827,723 B2 | 12/2004 | Carson | |
| 6,887,247 B1 | 5/2005 | Couture et al. | |
| 6,905,514 B2 | 6/2005 | Carignan et al. | |
| 6,923,817 B2 | 8/2005 | Carson et al. | |
| 6,923,831 B2 | 8/2005 | Fell et al. | |
| 6,932,842 B1 | 8/2005 | Litschko et al. | |
| 6,942,475 B2 | 9/2005 | Ensign et al. | |
| 6,944,518 B2 | 9/2005 | Roose | |
| 6,945,976 B2 | 9/2005 | Ball et al. | |
| 6,953,480 B2 | 10/2005 | Mears et al. | |
| 6,960,216 B2 | 11/2005 | Kolb et al. | |
| 6,990,220 B2 | 1/2006 | Ellis et al. | |
| 7,029,479 B2 | 4/2006 | Tallarida et al. | |
| 7,042,222 B2 | 5/2006 | Zheng et al. | |
| 7,048,741 B2 | 5/2006 | Swanson | |
| 7,050,877 B2 | 5/2006 | Iseki et al. | |
| 7,060,074 B2* | 6/2006 | Rosa et al. | 606/88 |
| 7,074,241 B2 | 7/2006 | McKinnon | |
| RE39,301 E | 9/2006 | Bertin | |
| 7,104,997 B2* | 9/2006 | Lionberger et al. | 606/88 |
| 7,105,026 B2 | 9/2006 | Johnson et al. | |
| 7,115,131 B2 | 10/2006 | Engh et al. | |
| 7,121,832 B2* | 10/2006 | Hsieh et al. | 434/262 |
| 7,141,053 B2 | 11/2006 | Rosa et al. | |
| 7,169,185 B2 | 1/2007 | Sidebotham | |
| 7,176,466 B2 | 2/2007 | Rousso et al. | |
| 7,184,814 B2 | 2/2007 | Lang et al. | |
| 7,198,628 B2 | 4/2007 | Ondrla et al. | |
| 7,218,232 B2 | 5/2007 | DiSilvestro et al. | |
| 7,239,908 B1 | 7/2007 | Alexander et al. | |
| 7,241,315 B2 | 7/2007 | Evans | |
| 7,255,702 B2 | 8/2007 | Serra et al. | |
| 7,258,701 B2 | 8/2007 | Aram et al. | |
| 7,275,218 B2 | 9/2007 | Petrella et al. | |
| 7,282,054 B2 | 10/2007 | Steffensmeier et al. | |
| 7,294,133 B2 | 11/2007 | Zink et al. | |
| 7,297,164 B2 | 11/2007 | Johnson et al. | |
| 7,309,339 B2 | 12/2007 | Cusick et al. | |
| 7,333,013 B2 | 2/2008 | Berger | |
| 7,335,231 B2 | 2/2008 | McLean | |
| 7,371,260 B2 | 5/2008 | Malinin | |
| 7,383,164 B2 | 6/2008 | Aram et al. | |
| 7,385,498 B2 | 6/2008 | Dobosz | |
| 7,388,972 B2 | 6/2008 | Kitson | |
| 7,392,076 B2 | 6/2008 | Moctezuma de La Barrera | |
| 7,427,200 B2 | 9/2008 | Noble et al. | |
| 7,427,272 B2 | 9/2008 | Richard et al. | |
| 7,468,075 B2 | 12/2008 | Lang et al. | |
| 7,474,223 B2 | 1/2009 | Nycz et al. | |
| 7,488,325 B2 | 2/2009 | Qian | |
| 7,494,510 B2 | 2/2009 | Zweymuller | |
| 7,517,365 B2 | 4/2009 | Carignan et al. | |
| 7,527,631 B2 | 5/2009 | Maroney et al. | |
| 7,534,263 B2 | 5/2009 | Burdulis, Jr. et al. | |
| 7,542,791 B2 | 6/2009 | Mire et al. | |
| 7,559,931 B2 | 7/2009 | Stone | |
| 7,575,602 B2 | 8/2009 | Amirouche et al. | |
| 7,578,851 B2 | 8/2009 | Dong et al. | |
| 7,582,091 B2 | 9/2009 | Duncan et al. | |
| 7,591,821 B2 | 9/2009 | Kelman | |
| 7,601,155 B2 | 10/2009 | Petersen | |
| 7,604,639 B2 | 10/2009 | Swanson | |
| 7,611,516 B2 | 11/2009 | Maroney | |
| 7,618,451 B2 | 11/2009 | Berez et al. | |
| 7,621,915 B2 | 11/2009 | Frederick et al. | |
| 7,625,409 B2 | 12/2009 | Saltzman et al. | |
| 7,646,161 B2 | 1/2010 | Albu-Schaffer et al. | |
| 7,651,501 B2 | 1/2010 | Penenberg et al. | |
| 7,670,345 B2 | 3/2010 | Plassky et al. | |
| 7,682,398 B2 | 3/2010 | Croxton et al. | |
| 7,695,477 B2 | 4/2010 | Creger et al. | |
| 7,695,521 B2 | 4/2010 | Ely et al. | |
| 7,699,847 B2 | 4/2010 | Sheldon et al. | |
| 7,704,253 B2 | 4/2010 | Bastian et al. | |
| 7,723,395 B2 | 5/2010 | Ringeisen et al. | |
| 7,780,672 B2 | 8/2010 | Metzger et al. | |
| 7,780,740 B2 | 8/2010 | Steinberg | |
| 7,794,466 B2 | 9/2010 | Merchant et al. | |
| 7,794,467 B2 | 9/2010 | McGinley et al. | |
| 7,794,504 B2 | 9/2010 | Case | |
| 7,806,896 B1 | 10/2010 | Bonutti | |
| 7,809,184 B2 | 10/2010 | Neubauer et al. | |
| 7,819,925 B2 | 10/2010 | King et al. | |
| 7,828,806 B2 | 11/2010 | Graf et al. | |
| 7,879,109 B2 | 2/2011 | Borden et al. | |
| 7,892,261 B2 | 2/2011 | Bonutti | |
| 7,896,922 B2 | 3/2011 | Smith et al. | |
| 7,935,119 B2* | 5/2011 | Ammann et al. | 606/87 |
| 7,935,150 B2 | 5/2011 | Carignan et al. | |
| 7,938,861 B2 | 5/2011 | King et al. | |
| 7,959,637 B2* | 6/2011 | Fox et al. | 606/88 |
| 7,962,196 B2 | 6/2011 | Tuma | |
| 7,963,968 B2 | 6/2011 | Dees, Jr. | |
| 7,967,823 B2* | 6/2011 | Ammann et al. | 606/88 |
| 7,967,868 B2 | 6/2011 | White et al. | |
| 7,974,677 B2 | 7/2011 | Mire et al. | |
| 7,981,158 B2 | 7/2011 | Fitz et al. | |
| 7,993,353 B2 | 8/2011 | Roßner et al. | |
| 8,062,301 B2* | 11/2011 | Ammann et al. | 606/87 |

(56) References Cited

U.S. PATENT DOCUMENTS

| | | | |
|---|---|---|---|
| 8,070,752 B2 | 12/2011 | Metzger et al. | |
| 8,083,745 B2 | 12/2011 | Lang et al. | |
| 8,083,746 B2 | 12/2011 | Novak | |
| 8,083,749 B2 * | 12/2011 | Taber | 606/96 |
| 8,086,336 B2 | 12/2011 | Christensen | |
| 8,092,465 B2 | 1/2012 | Metzger et al. | |
| 8,133,230 B2 * | 3/2012 | Stevens et al. | 606/87 |
| 8,133,234 B2 | 3/2012 | Meridew et al. | |
| 8,137,406 B2 * | 3/2012 | Novak et al. | 623/20.32 |
| 8,167,951 B2 * | 5/2012 | Ammann et al. | 623/20.32 |
| 8,170,641 B2 | 5/2012 | Belcher | |
| 8,182,489 B2 * | 5/2012 | Horacek | 606/87 |
| 8,192,441 B2 * | 6/2012 | Collazo | 606/87 |
| 8,192,495 B2 * | 6/2012 | Simpson et al. | 623/17.15 |
| 8,211,112 B2 * | 7/2012 | Novak et al. | 606/87 |
| 8,241,292 B2 * | 8/2012 | Collazo | 606/87 |
| 8,241,293 B2 * | 8/2012 | Stone et al. | 606/87 |
| 8,265,790 B2 * | 9/2012 | Amiot et al. | 700/245 |
| 8,282,646 B2 | 10/2012 | Schoenefeld et al. | |
| 8,298,237 B2 | 10/2012 | Schoenefeld et al. | |
| 8,303,596 B2 * | 11/2012 | Plaßky et al. | 606/87 |
| 8,333,772 B2 * | 12/2012 | Fox et al. | 606/88 |
| 8,355,773 B2 * | 1/2013 | Leitner et al. | 600/424 |
| 2001/0005797 A1 | 6/2001 | Barlow et al. | |
| 2001/0011190 A1 | 8/2001 | Park | |
| 2001/0054478 A1 | 12/2001 | Watanabe et al. | |
| 2002/0007294 A1 | 1/2002 | Bradbury et al. | |
| 2002/0029045 A1 | 3/2002 | Bonutti | |
| 2002/0052606 A1 | 5/2002 | Bonutti | |
| 2002/0059049 A1 | 5/2002 | Bradbury et al. | |
| 2002/0082741 A1 | 6/2002 | Mazumder et al. | |
| 2002/0087274 A1 | 7/2002 | Alexander et al. | |
| 2002/0107522 A1 | 8/2002 | Picard et al. | |
| 2002/0128872 A1 | 9/2002 | Giammattei | |
| 2002/0147415 A1 | 10/2002 | Martelli | |
| 2003/0009171 A1 | 1/2003 | Tornier | |
| 2003/0009234 A1 | 1/2003 | Treacy et al. | |
| 2003/0011624 A1 | 1/2003 | Ellis | |
| 2003/0018338 A1 | 1/2003 | Axelson et al. | |
| 2003/0039676 A1 | 2/2003 | Boyce et al. | |
| 2003/0055502 A1 | 3/2003 | Lang et al. | |
| 2003/0105526 A1 | 6/2003 | Bryant et al. | |
| 2003/0109784 A1 | 6/2003 | Loh et al. | |
| 2003/0120276 A1 | 6/2003 | Tallarida et al. | |
| 2003/0139817 A1 | 7/2003 | Tuke et al. | |
| 2003/0158606 A1 | 8/2003 | Coon et al. | |
| 2003/0171757 A1 | 9/2003 | Coon et al. | |
| 2003/0216669 A1 | 11/2003 | Lang et al. | |
| 2004/0018144 A1 | 1/2004 | Briscoe | |
| 2004/0030245 A1 | 2/2004 | Noble et al. | |
| 2004/0054372 A1 | 3/2004 | Corden et al. | |
| 2004/0068187 A1 | 4/2004 | Krause et al. | |
| 2004/0092932 A1 | 5/2004 | Aubin et al. | |
| 2004/0098133 A1 | 5/2004 | Carignan et al. | |
| 2004/0102852 A1 | 5/2004 | Johnson et al. | |
| 2004/0102866 A1 | 5/2004 | Harris et al. | |
| 2004/0106926 A1 | 6/2004 | Leitner et al. | |
| 2004/0115586 A1 | 6/2004 | Andreiko et al. | |
| 2004/0122439 A1 | 6/2004 | Dwyer et al. | |
| 2004/0128026 A1 | 7/2004 | Harris et al. | |
| 2004/0133276 A1 | 7/2004 | Lang et al. | |
| 2004/0138754 A1 | 7/2004 | Lang et al. | |
| 2004/0143336 A1 | 7/2004 | Burkinshaw | |
| 2004/0147927 A1 | 7/2004 | Tsougarakis et al. | |
| 2004/0148026 A1 | 7/2004 | Bonutti | |
| 2004/0153079 A1 | 8/2004 | Tsougarakis et al. | |
| 2004/0153087 A1 * | 8/2004 | Sanford et al. | 606/88 |
| 2004/0158254 A1 | 8/2004 | Eisermann | |
| 2004/0162619 A1 | 8/2004 | Blaylock et al. | |
| 2004/0167390 A1 | 8/2004 | Alexander et al. | |
| 2004/0171924 A1 | 9/2004 | Mire et al. | |
| 2004/0172137 A1 | 9/2004 | Blaylock et al. | |
| 2004/0181144 A1 | 9/2004 | Cinquin et al. | |
| 2004/0204644 A1 | 10/2004 | Tsougarakis et al. | |
| 2004/0204760 A1 | 10/2004 | Fitz et al. | |
| 2004/0212586 A1 | 10/2004 | Denny | |
| 2004/0220583 A1 | 11/2004 | Pieczynski et al. | |
| 2004/0236341 A1 | 11/2004 | Petersen | |
| 2004/0236424 A1 | 11/2004 | Berez et al. | |
| 2004/0243481 A1 | 12/2004 | Bradbury et al. | |
| 2004/0254584 A1 | 12/2004 | Sarin et al. | |
| 2004/0260301 A1 | 12/2004 | Lionberger et al. | |
| 2005/0008887 A1 | 1/2005 | Haymann et al. | |
| 2005/0010227 A1 | 1/2005 | Paul | |
| 2005/0010300 A1 | 1/2005 | Disilvestro et al. | |
| 2005/0015022 A1 | 1/2005 | Richard et al. | |
| 2005/0019664 A1 | 1/2005 | Matsumoto | |
| 2005/0027303 A1 | 2/2005 | Lionberger et al. | |
| 2005/0027361 A1 | 2/2005 | Reiley | |
| 2005/0043806 A1 | 2/2005 | Cook et al. | |
| 2005/0043837 A1 | 2/2005 | Rubbert et al. | |
| 2005/0049524 A1 | 3/2005 | Lefevre et al. | |
| 2005/0049603 A1 | 3/2005 | Calton et al. | |
| 2005/0059873 A1 | 3/2005 | Glozman et al. | |
| 2005/0060040 A1 | 3/2005 | Auxepaules et al. | |
| 2005/0065628 A1 | 3/2005 | Roose | |
| 2005/0070897 A1 | 3/2005 | Petersen | |
| 2005/0071015 A1 | 3/2005 | Sekel | |
| 2005/0075641 A1 * | 4/2005 | Singhatat et al. | 606/86 |
| 2005/0096535 A1 | 5/2005 | de la Barrera | |
| 2005/0113841 A1 | 5/2005 | Sheldon et al. | |
| 2005/0113846 A1 | 5/2005 | Carson | |
| 2005/0119664 A1 | 6/2005 | Carignan et al. | |
| 2005/0131662 A1 | 6/2005 | Ascenzi et al. | |
| 2005/0137708 A1 | 6/2005 | Clark | |
| 2005/0148843 A1 | 7/2005 | Roose | |
| 2005/0149042 A1 | 7/2005 | Metzger | |
| 2005/0171545 A1 | 8/2005 | Walsh et al. | |
| 2005/0177245 A1 | 8/2005 | Leatherbury et al. | |
| 2005/0203536 A1 | 9/2005 | Laffargue et al. | |
| 2005/0203540 A1 | 9/2005 | Broyles | |
| 2005/0216305 A1 | 9/2005 | Funderud | |
| 2005/0222573 A1 | 10/2005 | Branch et al. | |
| 2005/0228393 A1 * | 10/2005 | Williams et al. | 606/87 |
| 2005/0234461 A1 | 10/2005 | Burdulis et al. | |
| 2005/0234465 A1 * | 10/2005 | McCombs et al. | 606/88 |
| 2005/0234468 A1 | 10/2005 | Carson | |
| 2005/0240195 A1 * | 10/2005 | Axelson et al. | 606/87 |
| 2005/0240267 A1 | 10/2005 | Randall et al. | |
| 2005/0244239 A1 | 11/2005 | Shimp | |
| 2005/0245934 A1 | 11/2005 | Tuke et al. | |
| 2005/0245936 A1 | 11/2005 | Tuke et al. | |
| 2005/0251147 A1 | 11/2005 | Novak | |
| 2005/0267353 A1 | 12/2005 | Marquart et al. | |
| 2005/0267485 A1 | 12/2005 | Cordes et al. | |
| 2005/0267584 A1 | 12/2005 | Burdulis et al. | |
| 2005/0273114 A1 * | 12/2005 | Novak | 606/88 |
| 2005/0283252 A1 | 12/2005 | Coon et al. | |
| 2005/0283253 A1 | 12/2005 | Coon et al. | |
| 2006/0004284 A1 | 1/2006 | Grunschlager et al. | |
| 2006/0015120 A1 | 1/2006 | Richard et al. | |
| 2006/0030853 A1 | 2/2006 | Haines | |
| 2006/0038520 A1 | 2/2006 | Negoro et al. | |
| 2006/0052725 A1 | 3/2006 | Santilli | |
| 2006/0058803 A1 | 3/2006 | Cuckler et al. | |
| 2006/0058884 A1 | 3/2006 | Aram et al. | |
| 2006/0058886 A1 | 3/2006 | Wozencroft | |
| 2006/0089621 A1 | 4/2006 | Fard | |
| 2006/0093988 A1 | 5/2006 | Swaelens et al. | |
| 2006/0094951 A1 | 5/2006 | Dean et al. | |
| 2006/0095044 A1 | 5/2006 | Grady et al. | |
| 2006/0100832 A1 | 5/2006 | Bowman | |
| 2006/0111722 A1 | 5/2006 | Bouadi | |
| 2006/0122616 A1 | 6/2006 | Bennett et al. | |
| 2006/0136058 A1 | 6/2006 | Pietrzak | |
| 2006/0142657 A1 | 6/2006 | Quaid et al. | |
| 2006/0155380 A1 | 7/2006 | Clemow et al. | |
| 2006/0161167 A1 | 7/2006 | Myers et al. | |
| 2006/0172263 A1 | 8/2006 | Quadling et al. | |
| 2006/0178497 A1 | 8/2006 | Gevaert et al. | |
| 2006/0184177 A1 | 8/2006 | Echeverri | |
| 2006/0184250 A1 | 8/2006 | Bandoh et al. | |
| 2006/0190086 A1 | 8/2006 | Clemow et al. | |
| 2006/0195111 A1 * | 8/2006 | Couture | 606/86 |

(56) References Cited

U.S. PATENT DOCUMENTS

| | | | |
|---|---|---|---|
| 2006/0195194 A1 | 8/2006 | Gunther | |
| 2006/0195198 A1 | 8/2006 | James | |
| 2006/0200158 A1* | 9/2006 | Farling et al. | 606/87 |
| 2006/0204932 A1 | 9/2006 | Haymann et al. | |
| 2006/0210644 A1 | 9/2006 | Levin | |
| 2006/0217808 A1 | 9/2006 | Novak et al. | |
| 2006/0235421 A1 | 10/2006 | Rosa et al. | |
| 2006/0241635 A1* | 10/2006 | Stumpo et al. | 606/87 |
| 2006/0241636 A1* | 10/2006 | Novak et al. | 606/87 |
| 2006/0271058 A1 | 11/2006 | Ashton et al. | |
| 2006/0276796 A1 | 12/2006 | Creger et al. | |
| 2006/0276797 A1 | 12/2006 | Botimer | |
| 2006/0287733 A1 | 12/2006 | Bonutti | |
| 2006/0293681 A1* | 12/2006 | Claypool et al. | 606/87 |
| 2007/0015995 A1 | 1/2007 | Lang et al. | |
| 2007/0016209 A1* | 1/2007 | Ammann et al. | 606/79 |
| 2007/0027680 A1 | 2/2007 | Ashley et al. | |
| 2007/0066917 A1 | 3/2007 | Hodorek et al. | |
| 2007/0073137 A1 | 3/2007 | Schoenefeld | |
| 2007/0083214 A1 | 4/2007 | Duncan et al. | |
| 2007/0083266 A1 | 4/2007 | Lang | |
| 2007/0100258 A1 | 5/2007 | Shoham et al. | |
| 2007/0100450 A1 | 5/2007 | Hodorek | |
| 2007/0100462 A1 | 5/2007 | Lang et al. | |
| 2007/0118055 A1 | 5/2007 | McCombs | |
| 2007/0118138 A1* | 5/2007 | Seo et al. | 606/87 |
| 2007/0118243 A1 | 5/2007 | Schroeder et al. | |
| 2007/0150068 A1 | 6/2007 | Dong et al. | |
| 2007/0156066 A1 | 7/2007 | McGinley et al. | |
| 2007/0156171 A1 | 7/2007 | Lang et al. | |
| 2007/0162038 A1 | 7/2007 | Tuke | |
| 2007/0162039 A1 | 7/2007 | Wozencroft | |
| 2007/0173946 A1 | 7/2007 | Bonutti | |
| 2007/0173948 A1 | 7/2007 | Meridew et al. | |
| 2007/0185498 A2 | 8/2007 | Lavallee | |
| 2007/0191962 A1 | 8/2007 | Jones et al. | |
| 2007/0198022 A1 | 8/2007 | Lang et al. | |
| 2007/0203430 A1 | 8/2007 | Lang et al. | |
| 2007/0203605 A1 | 8/2007 | Melton et al. | |
| 2007/0219639 A1 | 9/2007 | Otto et al. | |
| 2007/0219640 A1 | 9/2007 | Steinberg | |
| 2007/0224238 A1 | 9/2007 | Mansmann et al. | |
| 2007/0226986 A1 | 10/2007 | Park et al. | |
| 2007/0233121 A1 | 10/2007 | Carson et al. | |
| 2007/0233136 A1 | 10/2007 | Wozencroft | |
| 2007/0233140 A1 | 10/2007 | Metzger et al. | |
| 2007/0233141 A1 | 10/2007 | Park et al. | |
| 2007/0233269 A1 | 10/2007 | Steines et al. | |
| 2007/0233272 A1 | 10/2007 | Boyce et al. | |
| 2007/0238069 A1 | 10/2007 | Lovald et al. | |
| 2007/0239282 A1 | 10/2007 | Caylor et al. | |
| 2007/0239481 A1 | 10/2007 | DiSilvestro et al. | |
| 2007/0244487 A1* | 10/2007 | Ammann et al. | 606/88 |
| 2007/0250169 A1 | 10/2007 | Lang | |
| 2007/0253617 A1 | 11/2007 | Arata et al. | |
| 2007/0255288 A1 | 11/2007 | Mahfouz et al. | |
| 2007/0255412 A1 | 11/2007 | Hajaj et al. | |
| 2007/0262867 A1 | 11/2007 | Westrick et al. | |
| 2007/0272747 A1 | 11/2007 | Woods et al. | |
| 2007/0276224 A1 | 11/2007 | Lang et al. | |
| 2007/0276400 A1 | 11/2007 | Moore et al. | |
| 2007/0276501 A1 | 11/2007 | Betz et al. | |
| 2007/0288029 A1* | 12/2007 | Justin et al. | 606/87 |
| 2007/0288030 A1* | 12/2007 | Metzger et al. | 606/87 |
| 2008/0009952 A1 | 1/2008 | Hodge | |
| 2008/0015599 A1 | 1/2008 | D'Alessio et al. | |
| 2008/0015603 A1* | 1/2008 | Collazo | 606/87 |
| 2008/0015604 A1* | 1/2008 | Collazo | 606/87 |
| 2008/0015605 A1* | 1/2008 | Collazo | 606/87 |
| 2008/0021299 A1 | 1/2008 | Meulink | |
| 2008/0021494 A1 | 1/2008 | Schmelzeisen-Redeker et al. | |
| 2008/0021567 A1 | 1/2008 | Meulink et al. | |
| 2008/0027563 A1 | 1/2008 | Johnson et al. | |
| 2008/0033442 A1 | 2/2008 | Amiot et al. | |
| 2008/0039850 A1* | 2/2008 | Rowley et al. | 606/87 |
| 2008/0051799 A1 | 2/2008 | Bonutti | |
| 2008/0051910 A1 | 2/2008 | Kammerzell et al. | |
| 2008/0058945 A1 | 3/2008 | Hajaj et al. | |
| 2008/0058947 A1 | 3/2008 | Earl et al. | |
| 2008/0062183 A1 | 3/2008 | Swaelens | |
| 2008/0065225 A1 | 3/2008 | Wasielewski et al. | |
| 2008/0097451 A1* | 4/2008 | Chen et al. | 606/88 |
| 2008/0112996 A1 | 5/2008 | Harlow et al. | |
| 2008/0114370 A1 | 5/2008 | Schoenefeld | |
| 2008/0133022 A1 | 6/2008 | Caylor | |
| 2008/0140081 A1* | 6/2008 | Heavener et al. | 606/87 |
| 2008/0140209 A1 | 6/2008 | Iannotti et al. | |
| 2008/0140213 A1* | 6/2008 | Ammann et al. | 623/20.32 |
| 2008/0146969 A1 | 6/2008 | Kurtz | |
| 2008/0147072 A1 | 6/2008 | Park et al. | |
| 2008/0147073 A1* | 6/2008 | Ammann et al. | 606/87 |
| 2008/0161815 A1 | 7/2008 | Schoenefeld et al. | |
| 2008/0161816 A1* | 7/2008 | Stevens et al. | 606/87 |
| 2008/0172125 A1 | 7/2008 | Ek | |
| 2008/0195099 A1 | 8/2008 | Minas | |
| 2008/0195107 A1 | 8/2008 | Cuckler et al. | |
| 2008/0195108 A1 | 8/2008 | Bhatnagar et al. | |
| 2008/0195109 A1* | 8/2008 | Hunter et al. | 606/87 |
| 2008/0195216 A1 | 8/2008 | Philipp | |
| 2008/0200926 A1 | 8/2008 | Verard et al. | |
| 2008/0208200 A1 | 8/2008 | Crofford | |
| 2008/0208353 A1 | 8/2008 | Kumar et al. | |
| 2008/0215059 A1 | 9/2008 | Carignan et al. | |
| 2008/0230422 A1 | 9/2008 | Pleil et al. | |
| 2008/0234664 A1 | 9/2008 | May et al. | |
| 2008/0234683 A1 | 9/2008 | May | |
| 2008/0234685 A1 | 9/2008 | Gjerde | |
| 2008/0234833 A1 | 9/2008 | Bandoh et al. | |
| 2008/0243127 A1 | 10/2008 | Lang et al. | |
| 2008/0255674 A1 | 10/2008 | Rahaman et al. | |
| 2008/0257363 A1 | 10/2008 | Schoenefeld et al. | |
| 2008/0262500 A1 | 10/2008 | Collazo | |
| 2008/0262624 A1 | 10/2008 | White et al. | |
| 2008/0269906 A1 | 10/2008 | Iannotti et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1* | 11/2008 | Kunz et al. | 606/87 |
| 2008/0294170 A1* | 11/2008 | O'Brien | 606/87 |
| 2008/0294266 A1 | 11/2008 | Steinberg | |
| 2008/0300600 A1 | 12/2008 | Guelat et al. | |
| 2008/0306485 A1* | 12/2008 | Coon et al. | 606/88 |
| 2008/0306558 A1 | 12/2008 | Hakki | |
| 2008/0312659 A1 | 12/2008 | Metzger et al. | |
| 2008/0319448 A1 | 12/2008 | Lavallee et al. | |
| 2009/0012526 A1 | 1/2009 | Fletcher | |
| 2009/0018546 A1 | 1/2009 | Daley | |
| 2009/0018666 A1 | 1/2009 | Grundei et al. | |
| 2009/0024131 A1 | 1/2009 | Metzger et al. | |
| 2009/0043556 A1 | 2/2009 | Axelson et al. | |
| 2009/0076371 A1 | 3/2009 | Lang et al. | |
| 2009/0076512 A1 | 3/2009 | Ammann et al. | |
| 2009/0076520 A1* | 3/2009 | Choi | 606/108 |
| 2009/0082770 A1 | 3/2009 | Worner et al. | |
| 2009/0082774 A1* | 3/2009 | Oti et al. | 606/87 |
| 2009/0087276 A1 | 4/2009 | Rose | |
| 2009/0088674 A1 | 4/2009 | Caillouette et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1* | 4/2009 | Aram et al. | 606/87 |
| 2009/0088760 A1* | 4/2009 | Aram et al. | 606/87 |
| 2009/0088761 A1 | 4/2009 | Roose et al. | |
| 2009/0088763 A1 | 4/2009 | Aram et al. | |
| 2009/0088865 A1 | 4/2009 | Brehm | |
| 2009/0088866 A1 | 4/2009 | Case | |
| 2009/0089034 A1 | 4/2009 | Penney et al. | |
| 2009/0089081 A1 | 4/2009 | Haddad | |
| 2009/0093815 A1 | 4/2009 | Fletcher et al. | |
| 2009/0093816 A1 | 4/2009 | Roose et al. | |
| 2009/0096613 A1 | 4/2009 | Westrick | |
| 2009/0099567 A1* | 4/2009 | Zajac | 606/79 |

(56) References Cited

U.S. PATENT DOCUMENTS

| | | |
|---|---|---|
| 2009/0105837 A1 | 4/2009 | Lafosse et al. |
| 2009/0118736 A1 | 5/2009 | Kreuzer |
| 2009/0118769 A1* | 5/2009 | Sixto et al. .................... 606/280 |
| 2009/0131941 A1 | 5/2009 | Park et al. |
| 2009/0131942 A1* | 5/2009 | Aker et al. ..................... 606/88 |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1* | 9/2009 | Park et al. ....................... 606/89 |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1* | 10/2009 | Amiot et al. ................... 606/130 |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1* | 11/2009 | Ammann et al. ............... 606/88 |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1* | 12/2009 | White et al. ..................... 606/70 |
| 2010/0010493 A1* | 1/2010 | Dower ............................ 606/87 |
| 2010/0016984 A1 | 1/2010 | Trabish |
| 2010/0016986 A1 | 1/2010 | Trabish |
| 2010/0023015 A1* | 1/2010 | Park ................................ 606/87 |
| 2010/0030231 A1 | 2/2010 | Revie et al. |
| 2010/0036404 A1 | 2/2010 | Yi et al. |
| 2010/0042105 A1* | 2/2010 | Park et al. ........................ 606/87 |
| 2010/0049195 A1* | 2/2010 | Park et al. ........................ 606/87 |
| 2010/0057088 A1* | 3/2010 | Shah .............................. 606/88 |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1* | 5/2010 | Couture et al. ................. 606/87 |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1* | 6/2010 | Jordan et al. .................... 606/88 |
| 2010/0152782 A1 | 6/2010 | Stone et al. |
| 2010/0160917 A1 | 6/2010 | Fitz et al. |
| 2010/0168752 A1* | 7/2010 | Edwards ......................... 606/87 |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1* | 7/2010 | White et al. .................... 606/88 |
| 2010/0198224 A1* | 8/2010 | Metzger et al. ................. 606/87 |
| 2010/0212138 A1* | 8/2010 | Carroll et al. .................. 29/446 |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1* | 8/2010 | Carroll et al. ............. 606/86 R |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1* | 12/2010 | Warne et al. .................... 606/87 |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1* | 1/2011 | Katrana et al. ................. 606/87 |
| 2011/0015639 A1* | 1/2011 | Metzger et al. ................. 606/91 |
| 2011/0015752 A1 | 1/2011 | Meridew |
| 2011/0022049 A1* | 1/2011 | Huebner et al. ................ 606/71 |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1* | 7/2011 | Stone et al. ..................... 606/88 |
| 2011/0172672 A1* | 7/2011 | Dubeau et al. .................. 606/87 |
| 2011/0184419 A1* | 7/2011 | Meridew et al. ................ 606/80 |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0251617 A1* | 10/2011 | Ammann et al. ............... 606/88 |
| 2011/0257657 A1 | 10/2011 | Turner et al. |
| 2011/0269100 A1* | 11/2011 | Furrer et al. ................... 433/72 |
| 2011/0275032 A1* | 11/2011 | Tardieu et al. ................ 433/174 |
| 2011/0295887 A1 | 12/2011 | Palmese et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0065640 A1 | 3/2012 | Metzger et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1* | 5/2012 | Meridew et al. ................ 606/91 |
| 2012/0109226 A1 | 5/2012 | Iannotti et al. |
| 2012/0130382 A1* | 5/2012 | Iannotti et al. ................. 606/87 |
| 2012/0136365 A1 | 5/2012 | Iannotti et al. |
| 2012/0141034 A1* | 6/2012 | Iannotti et al. ................ 382/199 |
| 2012/0143197 A1* | 6/2012 | Lang et al. ...................... 606/87 |
| 2012/0143267 A1* | 6/2012 | Iannotti et al. ............. 606/86 R |
| 2012/0209276 A1 | 8/2012 | Schuster |
| 2012/0215225 A1* | 8/2012 | Philippon et al. .............. 606/87 |
| 2012/0221017 A1* | 8/2012 | Bonutti ........................ 606/130 |
| 2012/0226283 A1 | 9/2012 | Meridew et al. |
| 2012/0232596 A1* | 9/2012 | Ribeiro ......................... 606/289 |
| 2012/0259335 A1* | 10/2012 | Scifert et al. ................... 606/80 |
| 2012/0265208 A1 | 10/2012 | Smith |
| 2012/0271314 A1* | 10/2012 | Stemniski et al. .............. 606/87 |
| 2012/0271366 A1 | 10/2012 | Katrana et al. |
| 2012/0276509 A1* | 11/2012 | Iannotti et al. ................ 434/267 |

(56) References Cited

U.S. PATENT DOCUMENTS

| | | | |
|---|---|---|---|
| 2012/0277751 A1 | 11/2012 | Catanzarite et al. | |
| 2012/0289965 A1* | 11/2012 | Gelaude et al. | 606/87 |
| 2012/0296339 A1* | 11/2012 | Iannotti et al. | 606/87 |
| 2012/0303004 A1* | 11/2012 | Uthgenannt et al. | 606/1 |
| 2012/0303033 A1* | 11/2012 | Weiner et al. | 606/87 |
| 2012/0310399 A1* | 12/2012 | Metzger | 700/98 |
| 2012/0316564 A1 | 12/2012 | Serbousek et al. | |
| 2012/0323246 A1 | 12/2012 | Catanzarite et al. | |
| 2013/0001121 A1 | 1/2013 | Metzger | |
| 2013/0006250 A1* | 1/2013 | Metzger et al. | 606/87 |
| 2013/0035766 A1* | 2/2013 | Meridew | 623/22.21 |
| 2013/0085500 A1* | 4/2013 | Meridew et al. | 606/89 |
| 2013/0110116 A1* | 5/2013 | Kehres et al. | 606/96 |
| 2013/0119579 A1* | 5/2013 | Iannotti et al. | 264/259 |
| 2013/0131681 A1* | 5/2013 | Katrana et al. | 606/87 |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182-CI | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A2 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |

(56) References Cited

FOREIGN PATENT DOCUMENTS

| WO | WO-2012116206 A1 | 8/2012 |
|---|---|---|
| WO | WO-2012158917 A1 | 11/2012 |
| WO | WO-2012173929 A1 | 12/2012 |
| WO | WO-2012174008 A1 | 12/2012 |

OTHER PUBLICATIONS

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) Sigma® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.

Botha, Charl P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazen, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

(56) References Cited

OTHER PUBLICATIONS

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

"Comprehensive®: Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use of Computerized Tomography in the Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478, filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

(56) References Cited

OTHER PUBLICATIONS

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability mailed Sep. 6, 2013 for PCT/US2012/026356 claiming benefit of U.S. Appl. No. 13/041,883, filed Mar. 7, 2011.

International Search Report and Written Opinion mailed Oct. 14, 2013 for PCT/US2013/057097 claiming benefit of U.S. Appl. No. 13/597,478, filed Aug. 29, 2012.

* cited by examiner

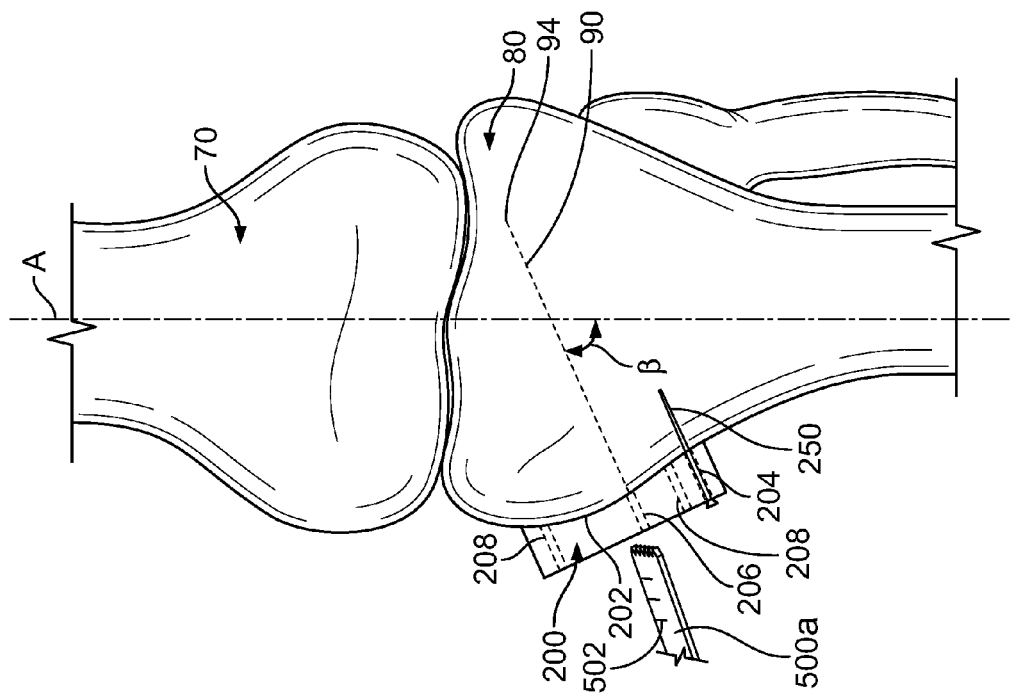
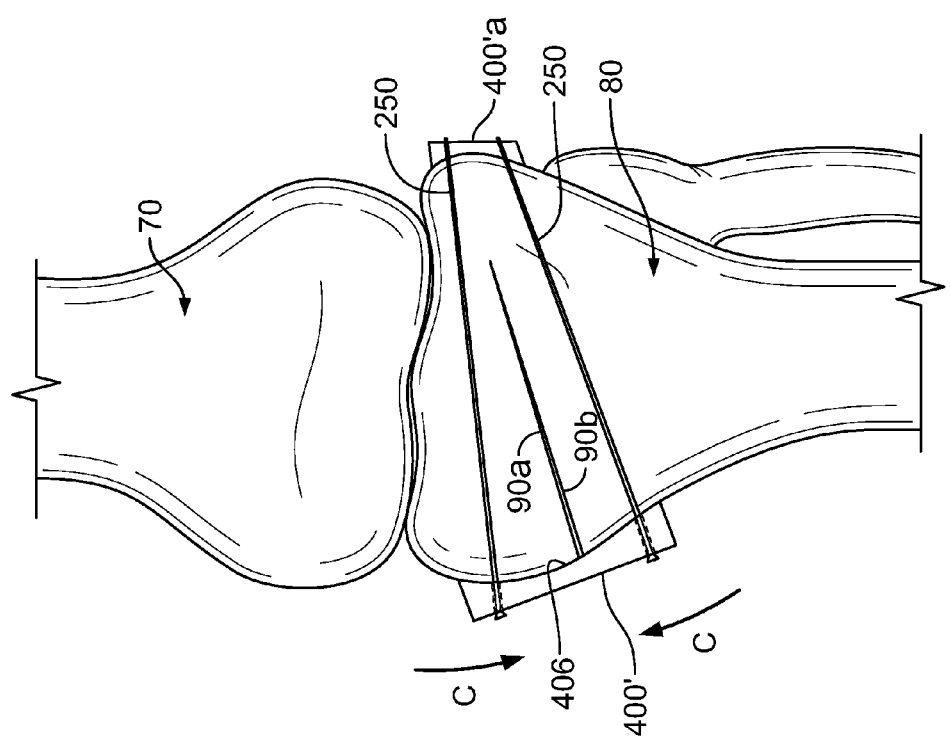

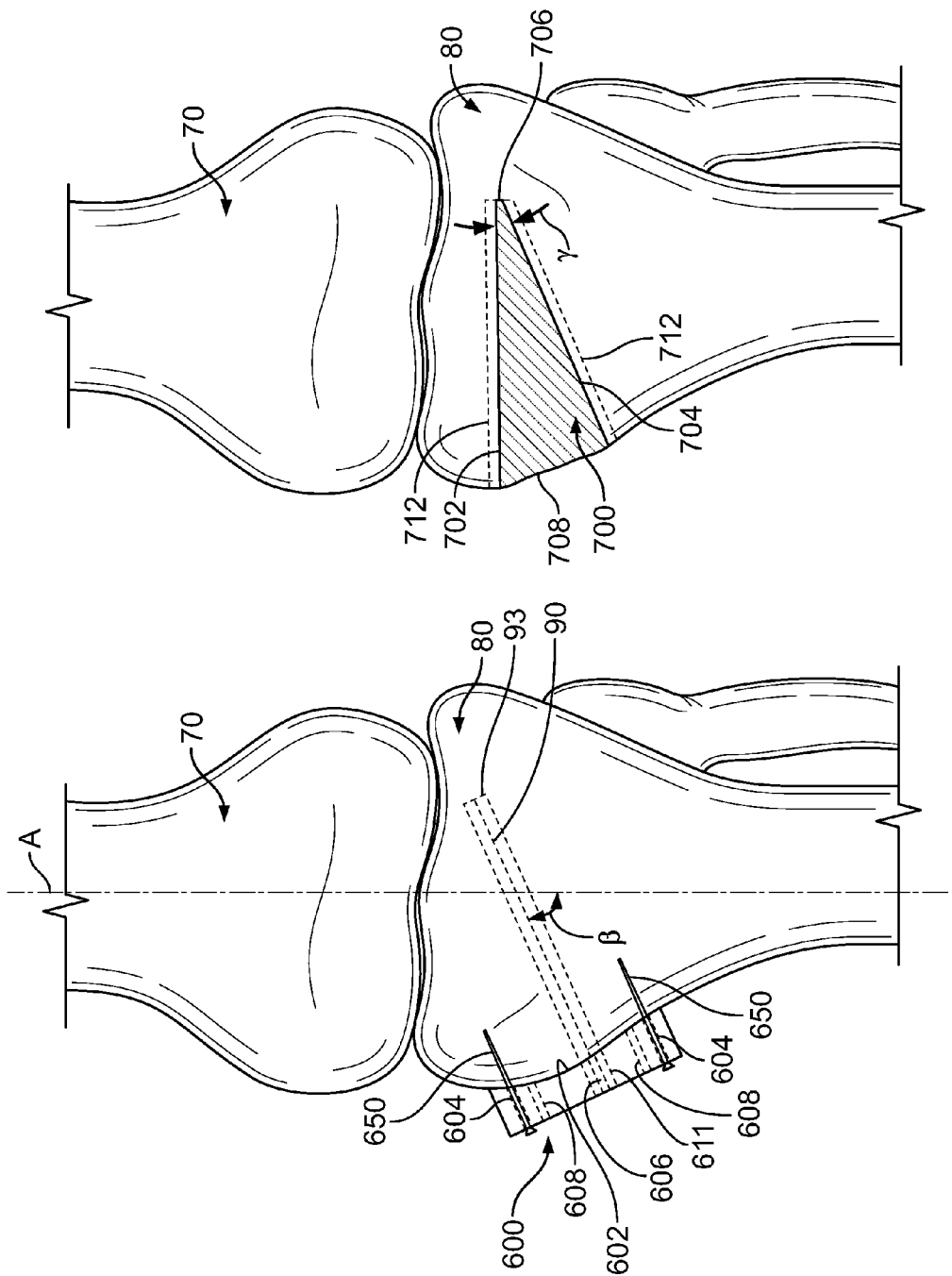

US 8,632,547 B2

PATIENT-SPECIFIC OSTEOTOMY DEVICES AND METHODS

CROSS-REFERENCE TO RELATED APPLICATIONS

This application is a continuation-in-part of U.S. application Ser. No. 12/714,023, filed Feb. 26, 2010. The disclosure of the above application is incorporated herein by reference.

INTRODUCTION

Various knee osteotomies are performed to adjust or change the orientation of the tibia to correct various abnormalities caused by birth defects, trauma, or disease. High tibial osteotomies include open-wedge and closed-wedge osteotomies. Various cutting instruments and tools are used to perform such high tibial osteotomies.

The present teachings provide patient-specific osteotomy implants and surgical instruments and associated methods for tibial osteotomies.

SUMMARY

The present teachings provide an osteotomy method and associated implants and instruments. The osteotomy method includes attaching a patient-specific osteotomy guide to a corresponding surface of a tibia of a patient and making an osteotomy at a patient-specific orientation through a resection slot of the osteotomy guide. The osteotomy guide is removed and first and second faces of the osteotomy are opened to form an implant insertion angle. The first and second faces of the osteotomy are secured at the implant insertion angle. An osteotomy implant having a patient-specific wedge angle that is smaller than the implant insertion angle is implanted. The first and second faces of the osteotomy are brought to the patient-specific wedge angle and in contact with the osteotomy implant.

The present teachings also provide an osteotomy surgical kit that includes a patient-specific osteotomy guide and a patient specific osteotomy implant. The osteotomy surgical kit can include a patient-specific spreader, a graduated osteotome and an osteotomy securing device for securing opposite faces of the osteotomy at a predetermined angle for implanting the osteotomy implant. The patient-specific osteotomy guide can include a patient-specific resection slot for guiding the resection and a drill support device for drilling a stress-relief hole at the edge of the osteotomy.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 5A is a schematic illustration of closing the wedge opening of FIG. 4 and attaching two fixation plates;

FIG. 6 is an environmental view of a patient-specific guide for an open-wedge high tibial osteotomy in relation to the present teachings;

FIG. 11 is an environmental view of the patient-specific guide of FIG. 10 according to present teachings;

FIG. 13 is an environmental view of the patient-specific implantable wedge according to present teachings;

Corresponding reference numerals indicate corresponding parts throughout the several views of the drawings.

DETAILED DESCRIPTION

Figure 1:
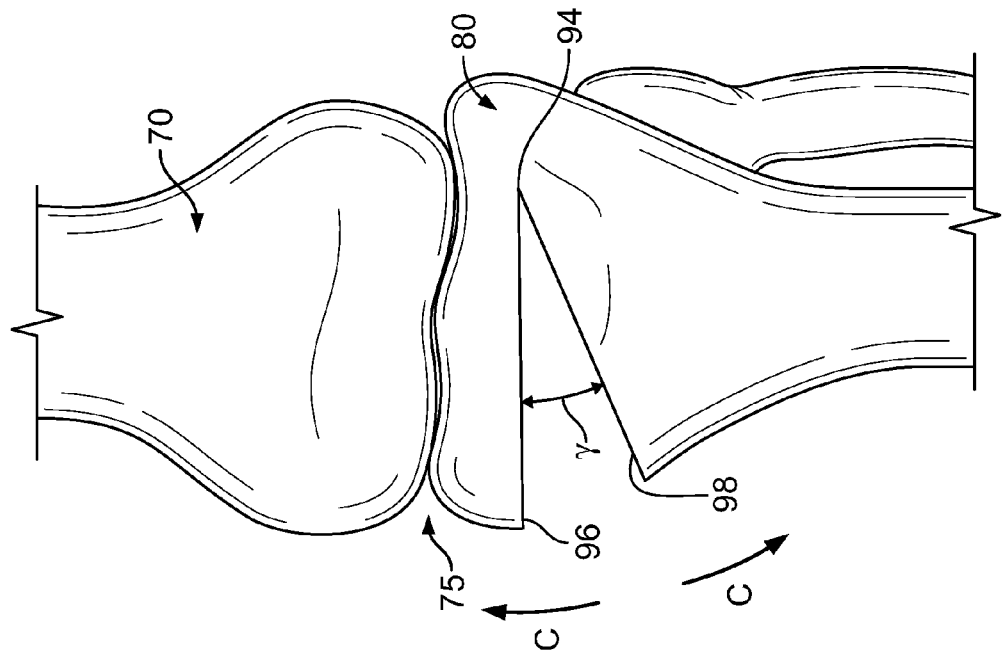
FIG. 1 is a schematic illustration of a cut for open-wedge high tibial osteotomy in relation to the present teachings.

The following description is merely exemplary in nature and is in no way intended to limit the present teachings, applications, or uses. For example, although the present teachings are illustrated for patient-specific instruments and implants for high tibial osteotomy, the present teachings can be used for other types of osteotomy procedures.

The present teachings generally provide patient-specific osteotomy surgical kits that include alignment guides and associated implant components for use in osteotomy, such as high tibial osteotomy, for example. The patient-specific alignment guides can be used either with conventional or patient-specific implant components prepared with computer-assisted image methods. Computer modeling for obtaining three dimensional images of the patient's anatomy using MRI or CT scans of the patient's anatomy, the patient specific prosthesis components, and the patient-specific guides and templates can be provided by various CAD programs and/or software available, for example, by Materialise USA, Plymouth, Mich.

The patient-specific alignment guides and associated patient-specific implants disclosed herein can be generally formed using computer modeling based on the patient's 3-D anatomic image generated from image scans. The patient-specific alignment guides can have a three-dimensional engagement surface that is made to conformingly contact and match a three-dimensional image of the patient's bone surface (selectively with or without soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan.

In various embodiments, the patient-specific alignment guide can include one or more patient-specific cutting guides for receiving and guiding a cutting blade at corresponding patient-specific cutting plane orientations relative to a selected anatomic axis for the specific patient. The patient-specific alignment guides can also include guiding formations for guiding the implantation of patient-specific or off-the-shelf implants associated with the osteotomy procedure, such as implantable wedges and implantable fixation plates. The geometry, shape and orientation of the various features of the patient-specific alignment guide, as well as various patient-specific implants and other patient-specific tools can be determined during the pre-operative planning stage of the procedure in connection with the computer-assisted modeling of the patient's anatomy. During the pre-operative planning stage, patient-specific alignment guides, implants and other tools, can be designed and manufactured for a specific patient with input from a surgeon or other professional associated with, the surgical procedure, as described in the commonly assigned and co-pending patent applications listed in the cross reference section and incorporated herein by reference.

In the following discussion, the terms "patient-specific", "custom-made" or "customized" are defined to apply to components, including tools, implants, portions or combinations thereof, which include certain geometric features, including surfaces, curves, or other lines, and which are made to closely conform as mirror-images or negatives of corresponding geometric features of a patient's anatomy during a pre-operative planning stage based on 3-D computer images of the corresponding anatomy reconstructed from image scans of the patient by computer imaging methods. Further, patient-specific guiding features, such as, guiding apertures and guiding slots, or other holes or openings that are included in alignment guides or in implants are defined as features that are made to have positions, orientations, dimensions, shapes and/or define cutting planes specific to the particular patient's anatomy based on the computer-assisted pre-operative plan associated with the patient.

Figure 3B:
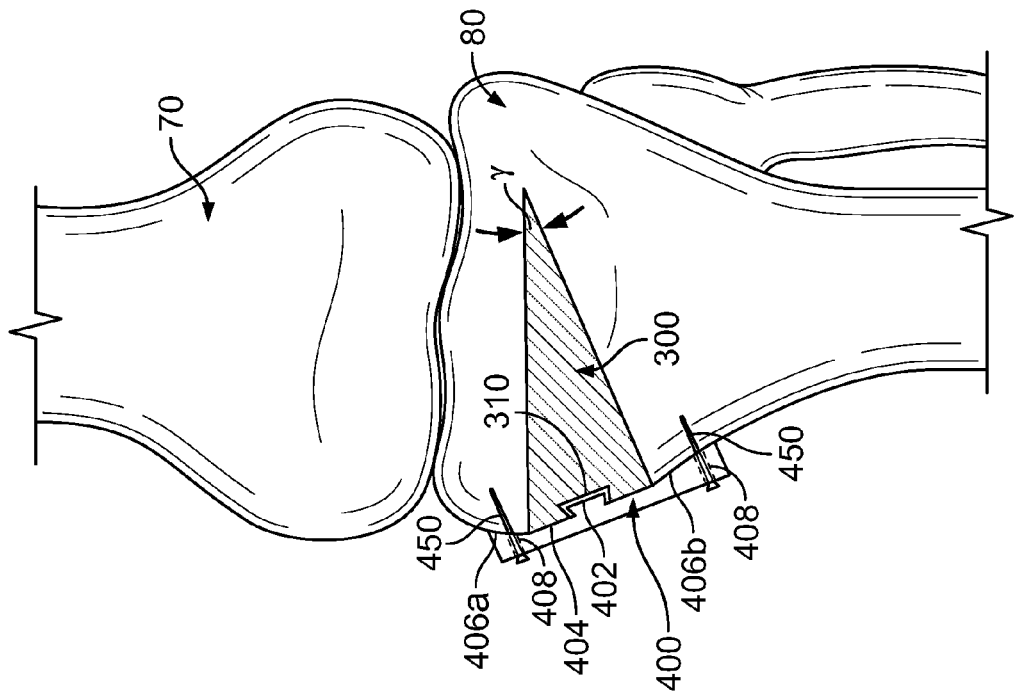
FIG. 3B is an environmental sectional view of a patient-specific plate and a patient-specific wedge of open-wedge high tibial osteotomy according to the present teachings.
Figure 3A:
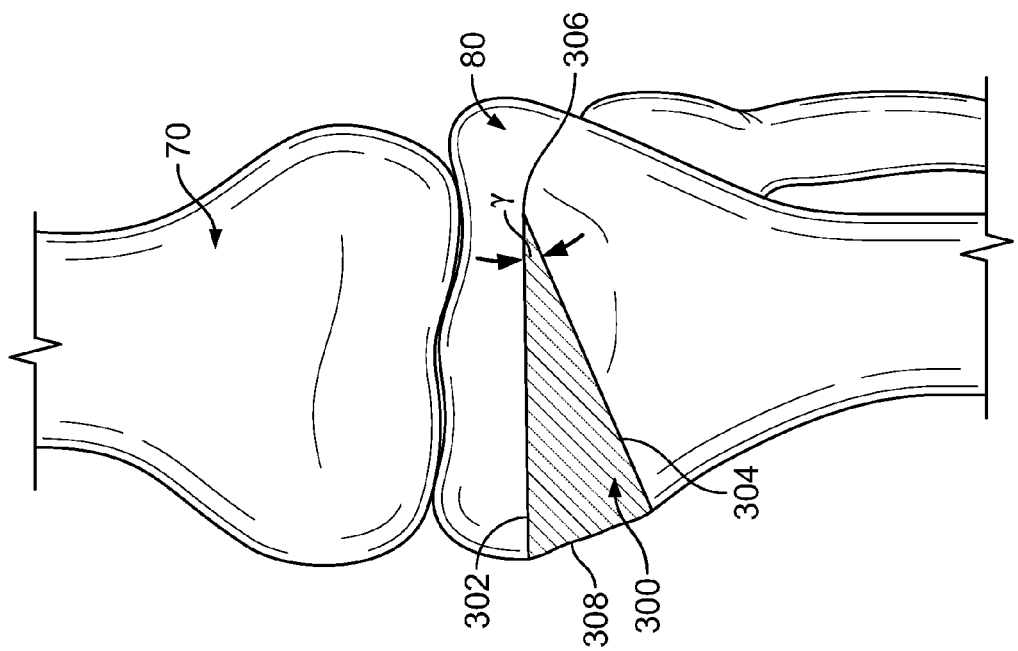
FIG. 3A is an environmental sectional view of a patient-specific wedge for the wedge opening of FIG. 2 according to the present teachings.
Figure 5:
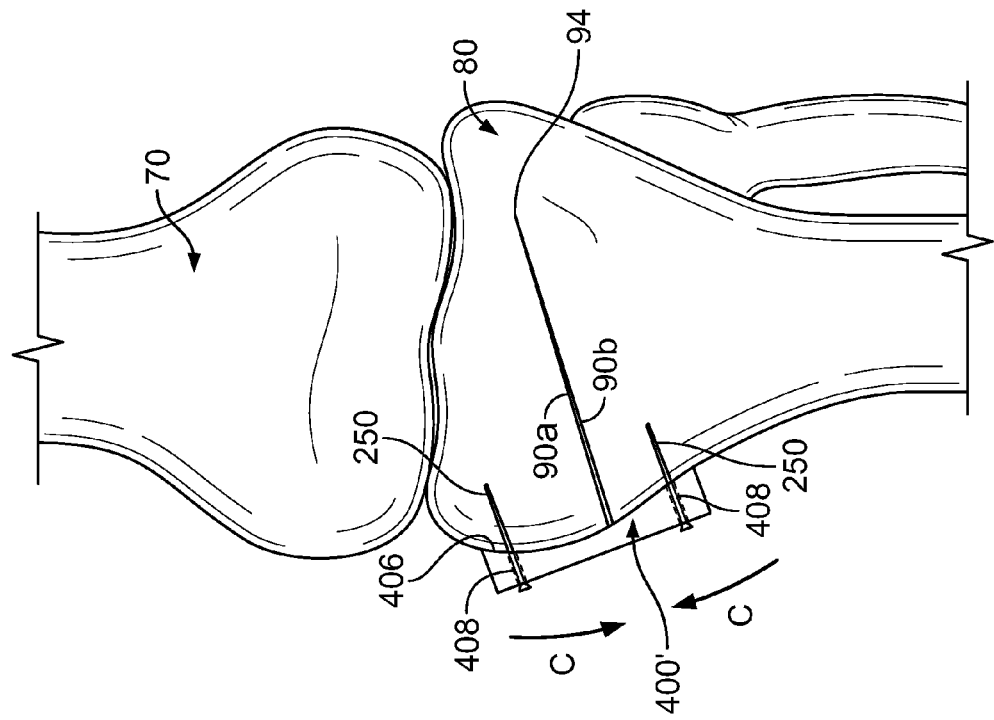
FIG. 5 is a schematic illustration of closing the wedge opening of FIG. 4 and attaching one fixation plate.

A patient-specific osteotomy kit for an open-wedge osteotomy can include, according to the present teachings, a patient-specific alignment guide 200, as shown in FIG. 6, for example, a patient-specific implantable wedge (or wedge implant) 300, as shown in FIGS. 3A-3B, for example, and a patient-specific implantable fixation plate 400, as shown in FIG. 5, for example. The implantable wedge 300 and a patient-specific implantable fixation plate 400 can be modularly connected, or alternatively formed monolithically as a single integral structure. An off-the-shelf, i.e. non patient-specific implantable wedge or an off-the-shelf, i.e. non patient-specific implantable fixation plate can also be used optionally with the patient-specific alignment guide 200. For closed-wedge osteotomies, the implantable wedge 300 is omitted. It will be appreciated that the patient-specific alignment guides for open-wedge and closed-wedge osteotomies can include different features, as discussed below.

The patient-specific osteotomy kit can also include custom-made saw blades 500a, 500b having a predetermined cutting length corresponding to a patient-specific cutting depth. The cutting depth can be determined at the pre-operative planning stage. In various embodiments, the predetermined cutting length can be an actual dimension of the cutting edge of the blade 500b (see FIG. 9). In various other embodiments, the cutting depth can be adjustable and the blade 500a can include markings 502 indicating a patient-specific cutting depth (see FIG. 6). The cutting depth can also be constrained by a depth stop engaging the patient-specific alignment guide 200 at a patient-specific depth and preventing insertion of the cutting blade beyond the pre-determined length. A separate, commercially available depth gauge can also be used to mark and restrict cutting to a pre-determined patient-specific cutting depth.

Figure 2:
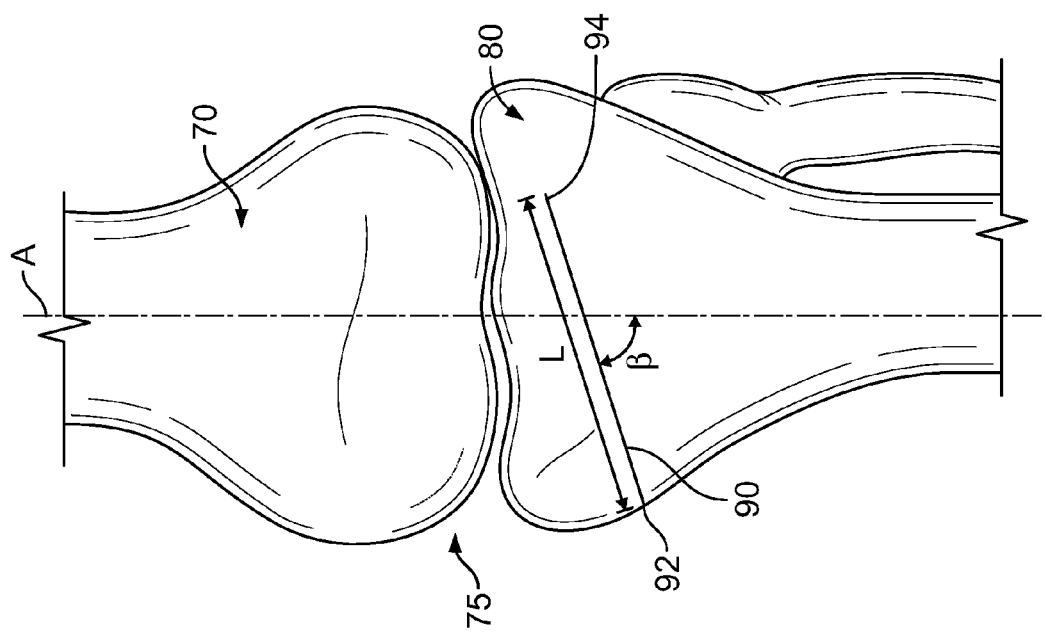
FIG. 2 is a schematic illustration of opening the cut of FIG. 1 to form an wedge opening.

Referring to FIGS. 1 and 2, an exemplary open-wedge high tibial osteotomy is illustrated in association with a knee joint 75 between a femur 70 and a tibia 80. A planar cut 90 at a selected angle β relative to a first reference axis A of the knee joint 75 can be made using the patient-specific kit of the present teachings. The first reference axis A can be a selected anatomic axis, such as, for example a mechanical axis of the joint or leg, a mechanical axis of the femoral bone, or a mechanical axis of the tibial bone, when different from the mechanical axis of the leg. Other anatomic axes, such as axes having significantly different orientations than the orientation of axis A illustrated in FIG. 1, can be used as reference axes, including, for example, an epicondylar axis, which can be substantially transverse to the axis A of FIG. 1. The angle β of the planar cut 90 relative to the reference axis A can be determined during the pre-operative planning stage of the osteotomy and in relation to the corresponding alignment guide 200.

Figure 1A:
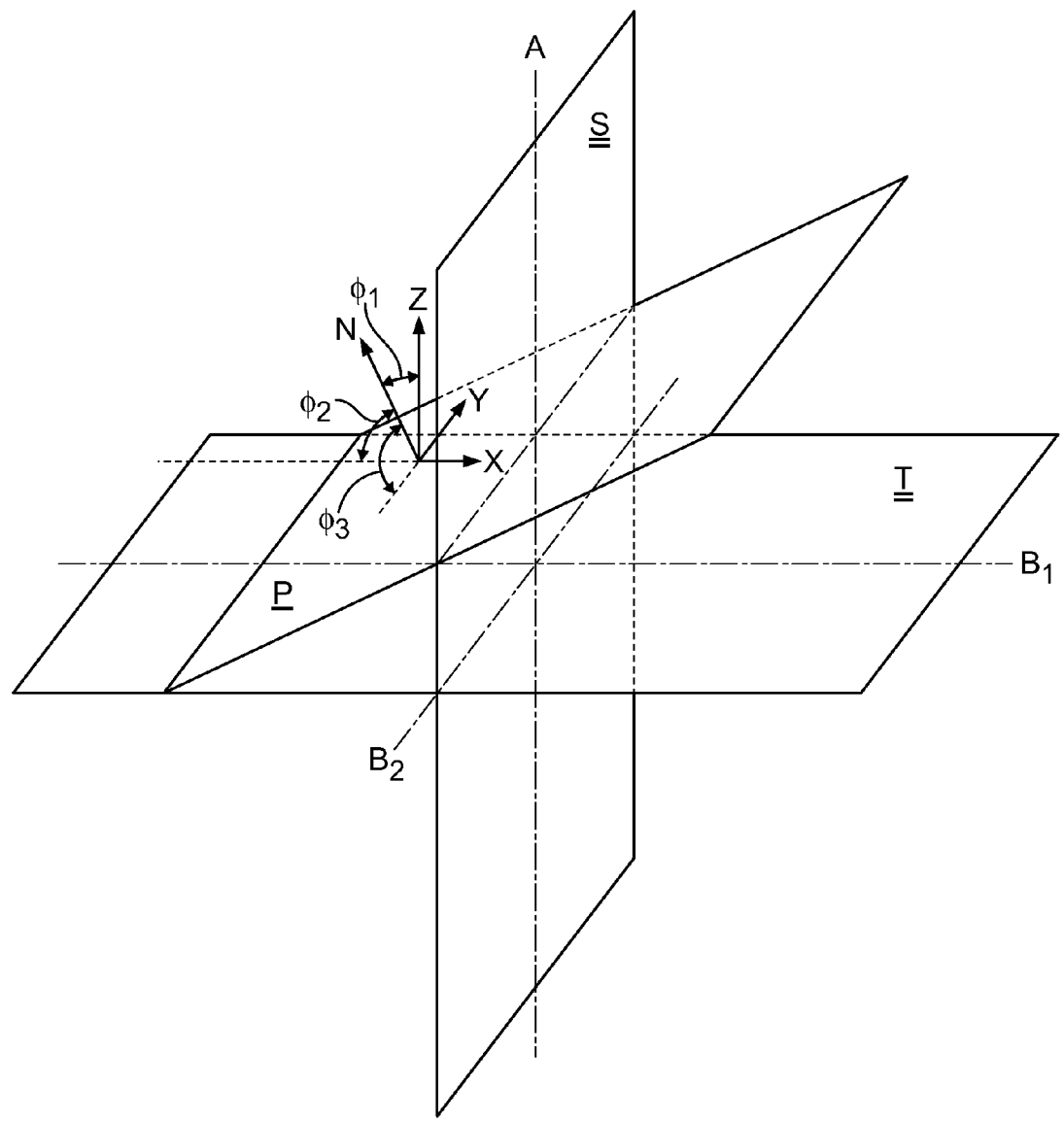
FIG. 1A is a schematic illustration of the geometry of an exemplary cut plane in relation to anatomic sagittal and transverse planes according to the present teachings.

The planar cut 90 can also be oriented at a patient-specific angle relative to second and third reference axes $B_1$ and $B_2$. A representative geometry illustrating the orientation of an exemplary cut plane P in relation to a sagittal plane S and a transverse plane T of the patient's anatomy is shown in FIG. 1A. In FIG. 1A, a first angle $\phi_1$ is defined between an axis N perpendicular to the cut plane P and an axis Z parallel to the first reference axis A, which extend superiorly-inferiorly on the sagittal plane. The first angle $\phi_1$ and angle β have a sum of 90 degrees. A second angle $\phi_2$ is defined between the axis N and an axis X parallel to the second reference axis $B_1$, which extends medially-laterally on the transverse plane T. A third angle $\phi_3$ is defined between the axis N and an axis Y parallel to the third reference axis $B_2$, which extends anteriorly-posteriorly on the transverse plane T. Medial-lateral, anterior-posterior and superior-inferior orientations of the cut plane P can be specified by selecting patient-specific values for these angles, keeping in mind that only two of the three angles can be specified independently, while the third can be calculated from the relation that the sum of the squares of the cosines of the angles is equal to 1. In the following discussion, although patient-specific orientations of planar cuts and corresponding planar slots relative to the axis A will be described in detail, it will be understood that the planar cuts and planar slots can be additionally or alternatively be oriented at patient-specific angles about the axes $B_1$ and $B_2$.

Referring to FIGS. 1-3, the planar cut 90 is a partial cut, i.e., not a through cut, and can extend from a first boundary 92 at the intersection of the planar cut 90 with the outer surface of the tibia 80 to a second boundary 94 at the selected patient-specific cutting depth illustrated as distance L in FIG. 1. The first boundary 92 can be generally a curved line reflecting the curvature of the outer surface of the tibia 80. The second boundary 94 can be substantially a straight line as formed by the saw blade. The second boundary 94 can function as a hinge line (also referenced with numeral 94) for opening a wedge or osteotomy angle γ between first and second opposing faces 96, 98 of the cut 90, as illustrated by arrows C in FIG. 2. The osteotomy angle γ is patient-specific and can be selected during the pre-operative planning stage. The location of the first and second boundaries 92, 94, the angle β of the planar cut 90 relative to the reference axis A and the wedge angle γ can be determined during the pre-operative planning stage for correcting a condition of the particular patient, including conditions resulting from idiopathic bone misalignment, joint or bone disease, trauma, cancer or other therapeutic or corrective surgery. Similarly, the planar cut 90 can be oriented at a corresponding patient-specific angle $\phi_2$ relative to the medial-lateral axis $B_1$, as illustrated in FIG. 1A.

Referring to FIGS. 1-3A, a patient-specific implantable wedge 300 having a corresponding wedge angle γ defined between first and second planar surfaces 302, 304 can be inserted and/or pushed between the first and second faces 96, 98 of the cut 90, while the cut 90 is partially open, i.e., while the first and second faces 96, 98 form an angle smaller than the angle γ, for guiding and facilitating the correct wedge opening to form the pre-selected angle γ. It will be appreciated, however, the cut 90 can be opened to an angle γ, using any other tool, such as trial wedge having the same angle γ. In some embodiments, the cut 90 is opened at an angle greater than γ, as discussed below in connection with FIGS. 20-23.

With continued reference to FIGS. 1-3A, the first and second planar surfaces 302, 304 of the implantable wedge 300 can meet at a straight edge or truncated plane surface 306. Upon insertion of the implantable wedge 300, the cut 90 is opened and secured to the selected angle γ by the implantable wedge 300. The first and second planar surfaces 302, 304 of the implantable wedge 300 can abut against the first and second faces 96, 98 of the planar cut 90, and the edge 306 of the implantable wedge 300 can abut the second boundary 94 of the planar cut 90. The implantable wedge 300 can have a patient-specific boundary surface 308 opposite to the edge/surface 306. The boundary surface 308 is designed during the pre-operative planning stage as a continuous and smooth surface that provides a continuous contour relative to the contour of the tibia 80 on either side of the cut 90. The implantable wedge 300 can also be secured directly in the bone with sutures, pins, anchors or other fasteners. In some embodiments, the implantable wedge can be cemented or coated with materials promoting bone in-growth.

Alternatively, and referring to FIGS. 3A and 3B, a patient-specific implantable fixation plate 400 can be used in combination with the patient-specific implantable wedge 300. The patient-specific implantable wedge 300 and the patient-specific fixation plate 400 can be modularly connected, as illustrated in FIG. 3B, or can be provided as a single monolithic and integrally formed component. A modular connection can include a dovetail connection illustrated at reference numerals 402 and 310 corresponding to opposing connection formations of the fixation plate 400 and implantable wedge 300. Other connection formations can include a taper lock connection, various groove and tongue connections, or connections with threadable fasteners or other biocompatible fasteners. The modular connection can be formed at a common boundary 404 between the fixation plate 400 and the implantable wedge 300.

The fixation plate 400 can include patient-specific surfaces 406a, 406b on either side the implantable wedge 300 and can be anchored to the tibia 80 using bone pins or other bone fasteners 450 that pass through corresponding apertures 408 of the fixation plate 400. The location and orientation of the apertures can also be patient-specific and determined during the pre-operative planning stage for the particular patient.

In various embodiments, and referring to FIG. 6, a patient-specific alignment guide 200 for an open-wedge osteotomy is illustrated. The alignment guide 200 can include a three-dimensional patient-specific engagement surface 202 made to conform to a corresponding outer surface of the tibia 80 by a computer-assisted method utilizing a 3-D image of the patient's tibia 80 during the pre-operative planning stage, as discussed above. The alignment guide 200 can include one or more guiding receptacles, the precise location of which is determined on the basis of a pre-operative surgical plan for locating alignment pins or other fasteners or for assisting in locating cutting blades or other cutting instruments for resecting the bone and/or shaping the bone for receiving an implant, as described in commonly-owned, co-pending in U.S. patent application Ser. No. 11/756,057, filed on May 31, 2007, incorporated herein by reference. The alignment guide can be placed on and conform with the anterior/lateral surface of the tibia, for example.

Referring to FIG. 6, the alignment guide 200 can include a guiding receptacle in the form of a planar slot 206 oriented to define a patient-specific angle β relative to the anatomic axis A for guiding a blade 500a to form the planar cut 90. The blade 500a can include depth-control indicia 502 corresponding to the hinge line 94. The alignment guide 200 can also define one or more fixation apertures 204 for receiving bone fixation fasteners 250. Additional guiding receptacles, such as guiding apertures 208, can be provided for preparing fastener holes in the tibia 80 to receive the bone fixation fasteners 250 through the apertures 408 of the fixation plate 400. The location and orientation of the planar slot 206, the apertures 204 for the fasteners 250 and the guiding apertures 208 relative to alignment guide 200 can be determined during the pre-operative planning stage on a patient-specific (patient customized) basis. Similarly, the planar slot 206 can be oriented at a corresponding patient-specific angle $\phi_2$ relative to the medial-lateral axis $B_1$, as illustrated in FIG. 1A.

Figure 8:
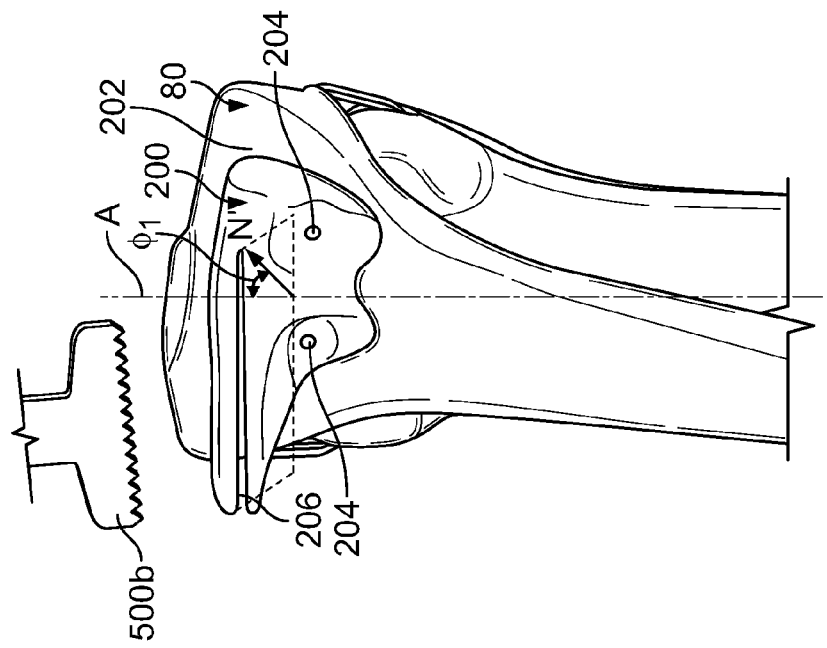
FIG. 8 is an environmental view of a patient-specific guide for an open-wedge high tibial osteotomy in relation to the present teachings.

Referring to FIG. 8, another alignment guide 200 for open-wedge osteotomy is illustrated. The alignment guide 200 can be placed on the anterior and/or lateral side of the proximal tibia 80, such that the three-dimensional patient-specific engagement surface 202 of the alignment guide 200 closely conforms to the corresponding portion of the tibia 80. The plane defined by the planar slot 206 is shown in phantom at a corresponding angle $\beta = 90 - \phi_1$ relative to the reference/anatomic axis A, as discussed above in connection with FIG. 6. A blade 500b can be used for the plane cut through the planar slot 206 having a size that provides automatic control of the length of the cut.

Figure 4:
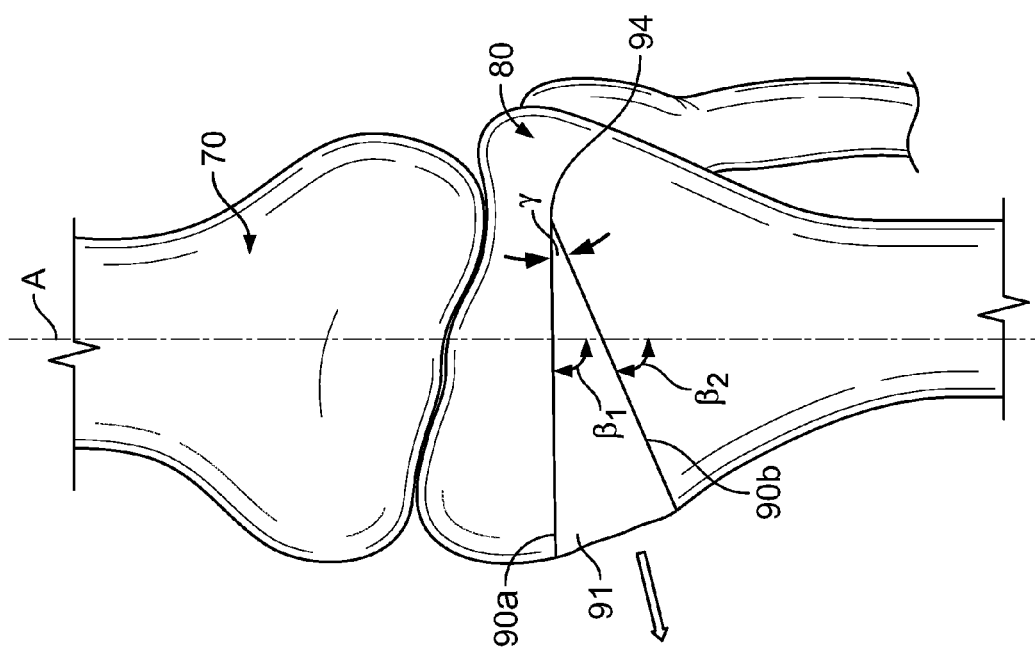
FIG. 4 is a schematic illustration of removing a bone wedge for closed-wedge high tibial osteotomy in relation to the present teachings.

Referring to FIGS. 4 and 5, an exemplary closed-wedge high tibial osteotomy is illustrated in association with a knee joint 75 between a femur 70 and a tibia 80. First and second partial planar cuts 90a, 90b at corresponding selected first and second angles $\beta_1$ and $\beta_2$ relative to a reference/anatomic axis A of the knee joint 75 can be made using a patient-specific kit of the present teachings. The first and second planar cuts 90a, 90b can intersect at a hinge line 94. The first and second angles $\beta_1$ and $\beta_2$ of the planar cuts 90a, 90b relative to the reference axis A can be determined during the pre-operative planning stage of the osteotomy and in relation to the corresponding alignment guide 200. Each of the first and second angles $\beta_1$ and $\beta_2$ is complementary of a corresponding angle $\phi_1$ shown in FIG. 1A (90-$\beta_1$ and 90-$\beta_2$). Similarly, the first and second cuts 90a, 90b can be oriented at corresponding and different angles $\phi_2$ relative to the medial-lateral axis $B_1$, as illustrated in FIG. 1A. The first and second angles $\beta_1$ and $\beta_2$ of the planar cuts 90a, 90b define a bone wedge 91 of predetermined wedge angle $\gamma = \beta_1 - \beta_2$. The bone wedge 91 can be removed and the corresponding wedge opening can be closed by bringing the surfaces of the first and second cuts 90a, 90b in contact by rotating about the hinge line 94. A first (or osteotomy-side) patient-specific fixation plate 400' can be attached to the tibia 80 to secure the first and second cuts 90a, 90b in contact after the bone wedge 91 is removed. The first and second cuts 90a, 90b can also be secured by pins, sutures or other fasteners to the bone. In the fixation plate 400' the same reference numerals are used to indicate features having the same functions as in the fixation plate 400. The fixation plate 400' can include a patient-specific engagement surface 406 and apertures 408 at patient-specific positions and orientations for guiding bone fixation fasteners 250 through the apertures 408 and into the tibia 80.

Referring to FIGS. 5 and 5A, a second (or hinge-side) fixation plate 400'a can be used opposite the first or osteotomy-side fixation plate 400' on the side of the osteotomy hinge. The second fixation plate 400'a can be a patient-specific fixation plate or an off-the shelf commercially available fixation plate. The second plate 400'a can be attached to the tibia with separate fasteners. Alternatively, the same fixation fasteners 250 can extend between both the first and second plates 400' and 400'a. In such case, the guiding apertures 208 of the alignment guide 200' can be used to drill guiding holes through the entire width of the tibia 80 for guiding the location of the first and second plates 400' and 400'a and the common fixation fasteners 250 through the tibia and through the first and second plates 400' and 400'a.

Figure 7:
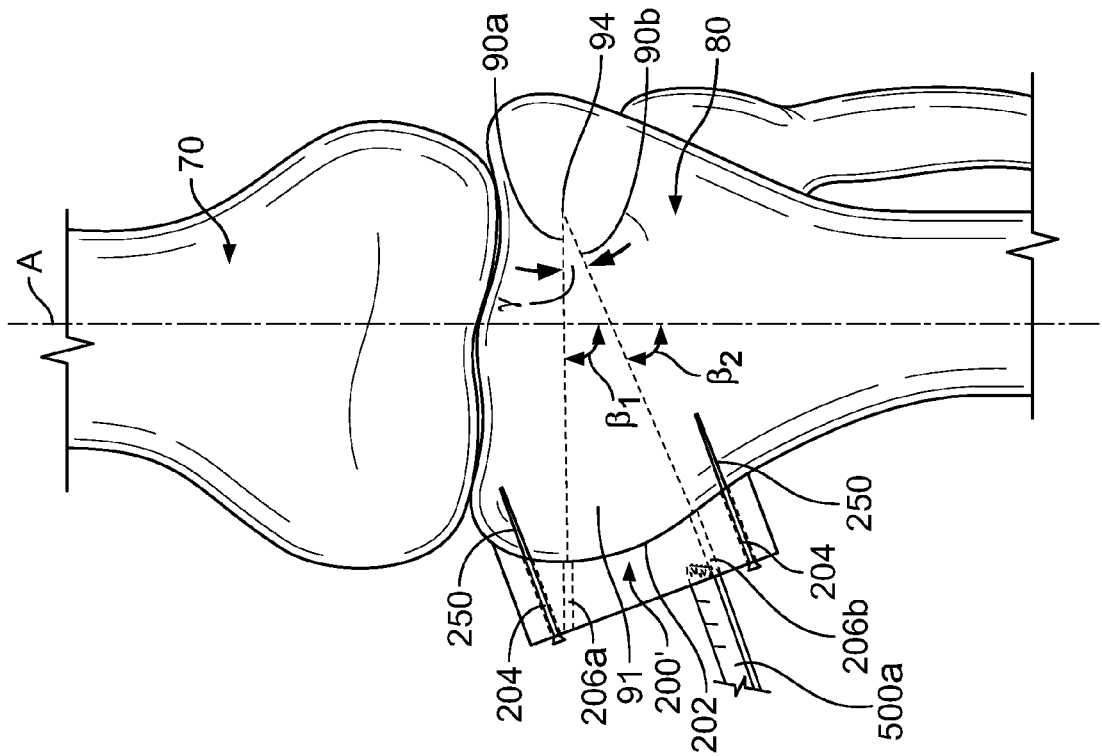
FIG. 7 is an environmental view of a patient-specific guide for closed-wedge high tibial osteotomy in relation to the present teachings.
Figure 10:
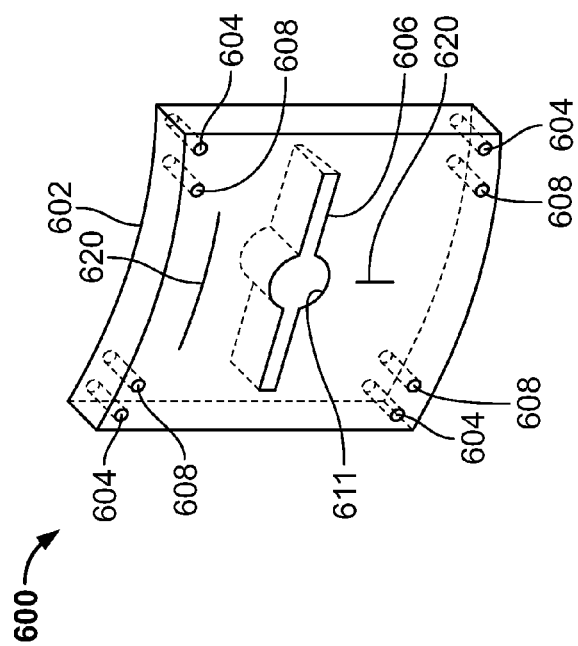
FIG. 10 is an isometric view of a patient-specific guide according to present teachings.

Referring to FIG. 7, a patient-specific alignment guide 200' for a closed-wedge osteotomy is illustrated. In alignment guide 200' the same reference numerals are used to indicate features having the same functions as in alignment guide 200. The alignment guide 200' can include a three-dimensional patient-specific engagement surface 202 made to conform to a corresponding outer surface of the tibia 80 by a computer-assisted method utilizing a 3-D image of the patient's tibia 80 during the pre-operative planning stage, as discussed above. The alignment guide 200' can define first and second guiding receptacles in the form of first and second planar slots 206a, 206b oriented at selected first and second angles $\beta_1$ and $\beta_2$ relative to a reference/anatomic axis A for guiding a blade to form the planar cuts 90a, 90b of the removable bone wedge 91. The alignment guide 200' can also define one or more apertures 204 receiving bone fixation fasteners 250. Additional guiding receptacles, such as guiding apertures 208 can be provided for drilling or otherwise preparing fastener holes in the tibia 80 corresponding to the apertures 408 of the fixation plate 400 for securing the fixation plate 400 to the tibia 80. The location and orientation of the first and second planar slots 206a, 206b, the apertures 204 and the guiding apertures 208 relative to alignment guide 200' can be determined during the pre-operative planning stage on a patient-specific base. The alignment guide 200' can be used with a blade 500a having depth indicia 502.

Figure 9:
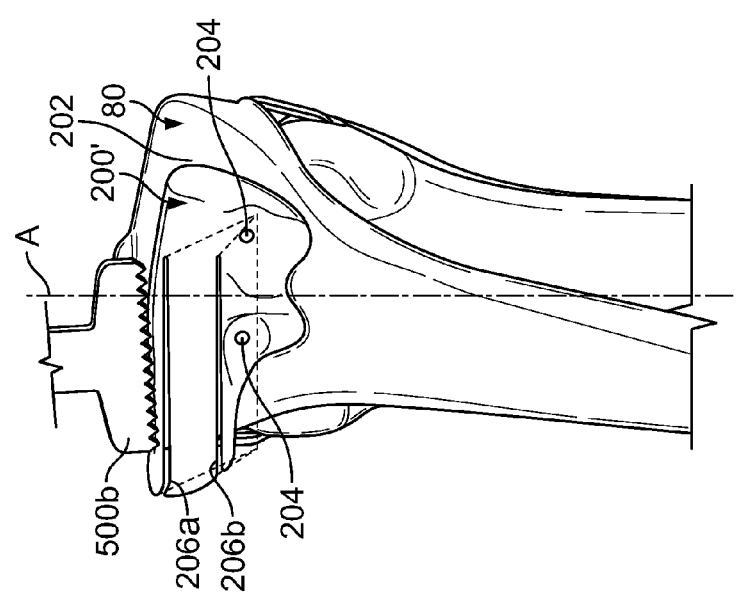
FIG. 9 is an environmental view of a patient-specific guide for closed-wedge high tibial osteotomy in relation to the present teachings.

Referring to FIG. 9, another alignment guide 200' for closed-wedge osteotomy is illustrated. The alignment guide 200' can be placed on the anterior and/or lateral side of the proximal tibia 80, such that the patient-specific engagement surface 202 of the alignment guide 200' closely conforms to the corresponding portion of the tibia 80. The planes defined by the first and second planar slots 206a, 206b are shown in phantom at corresponding first and second angles $\beta_1$ and $\beta_2$ (not shown) relative to the reference/anatomic axis A, as discussed above in connection with FIG. 7 and FIG. 1A. Additionally and optionally, each of the first and second angles $\beta_1$ and $\beta_2$ is complementary of a corresponding angle $\phi_1$ shown in FIG. 1A (90-$\beta_1$ and 90-$\beta_2$). Similarly, the planes defined by the first and second planar slots 206a, 206b can be oriented at corresponding and different angles $\phi_2$ relative to the medial-lateral axis $B_1$, as illustrated in FIG. 1A.

Referring to FIGS. 10-13, another embodiment of a patient-specific alignment guide is illustrated at 600. As in the embodiments discussed above, the patient-specific alignment guide includes a three-dimensional patient-specific engagement surface 602, fixation apertures 604 for bone fixation fasteners 650 and guiding apertures 608 for drilling holes in the bone. In this embodiment, the alignment guide 600 includes a central cylindrical through-hole 611 passing through the center of a planar slot 606. The central hole 611, which has a diameter greater than the opening of the slot 606, can facilitate cutting with a blade along the slot 606 through either side of the central hole 611. Referring to FIG. 11, the central hole 611 of the alignment guide 600 can be used to drill a hole 93 in the bone 80 before the planar osteotomy cut 90 is performed at a selected patient-specific angle $\beta$, as shown in FIG. 11. The patient-specific guide 600 can include radiopaque markers 620, which are visible in radiographic images and can provide directional guidance during the surgical procedure. Similar markers in the form of lines or points/spots can also be provided on the patient-specific alignment guides 200, 200' discussed above.

Figure 12:
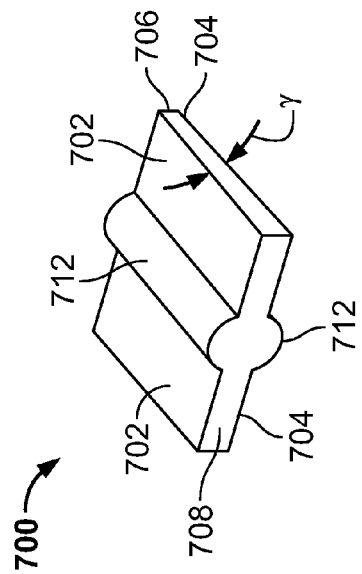
FIG. 12 is an isometric view of an exemplary implantable wedge according to present teachings.

Referring to FIGS. 12 and 13, a patient-specific implantable wedge 700 can be inserted through the osteotomy cut to keep the osteotomy open. Similarly to the embodiments described above, the implantable wedge 700 can include a three-dimensional patient-specific surface 708 (best shown in FIG. 13), an elongated curved central portion 712 conforming to shape of the drilled hole 93 on the opposite surfaces of the planar cut 90. The elongated central portion 712 can be cylindrical or tapered (truncated cone or conical segment). A pair of planar portions 702, 704 extends radially from opposite sides of the central portion 712 from the patient specific surface 708 to an end surface 706 and defines a wedge of angle γ. The central portion 712 can be aligned with the hole 93 and provide a guide for centering and inserting the implantable wedge 700 into the osteotomy cut 90. The central portion 712 can have greater thickness than and protrude away from and outside the planar portions 702, 704.

Figure 14A:
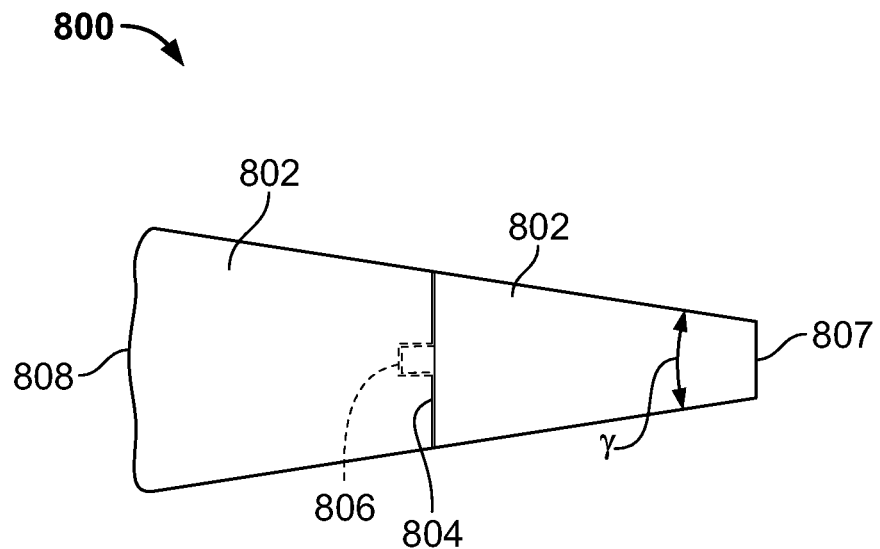
FIGS. 14A and 14B are plan views of exemplary implantable wedges according to present teachings.
Figure 14B:
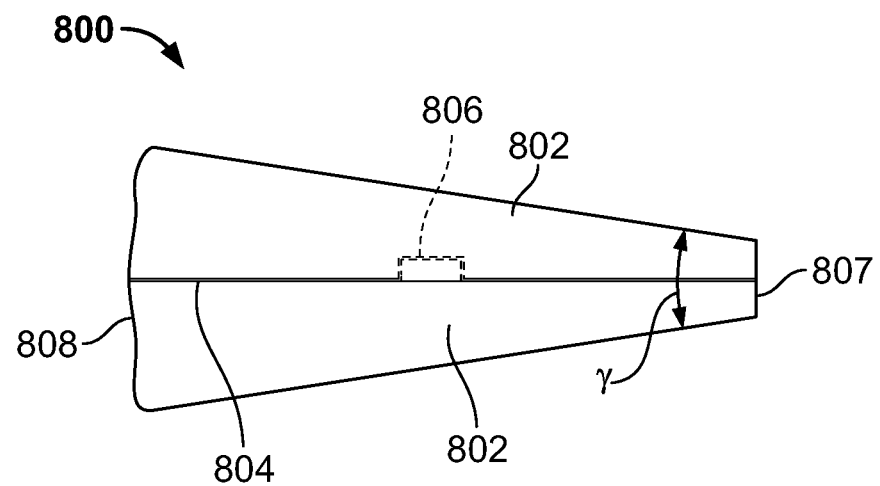

The various patient-specific implantable wedges 300, 700 for the open-wedge osteotomy can be made of various biocompatible materials including, for example, various solid metals or alloys, solid PEEK, porous metal and porous metal alloys, porous thermoplastics, such as PEEK (polyether ether ketone), PEKK (polyether ketone ketone), osteoinductive or osteoconductive materials, including Pro Osteon®, commercially available from Biomet, Inc., Warsaw, Ind., with or without a resorbable filler material, and/or combinations thereof. The implantable wedges 300, 700 can also be in the form of multiple-component wedges with or without interlocking connecting features. An exemplary illustration of a multiple-piece implantable wedge 800 is shown in FIGS. 14A and 14B. The implantable wedge 800 can extend from a first surface 808 to a second surface 807. The first surface 808 can be optionally patient-specific. The implantable wedge 800 can include a plurality of separate components 802. Two adjacent components 802 can be in contact at a common boundary 804. The adjacent components 802 can also be optionally interlocked with a connecting feature 806. The connecting feature 806 can be a single structural connector or a plurality of structural connectors, including tongue and groove, interdigitation, dovetail, threaded fasteners, etc.

The various fixation plates 400, 400', 400'a can be made of similar materials. For open-wedge osteotomies, the fixation plate 400 can be integral to the implantable wedge 300, modularly coupled to the implantable wedge 300 via a connecting joint or fasteners, or directly coupled to the bone outside the implantable wedge 300. The various alignment guides 200, 200', 600 can be made of any biocompatible material, including, polymer, ceramic, metal or combinations thereof.

As discussed above in connection with FIGS. 1-14B, a surgical kit for an open-wedge or a closed-wedge high tibial osteotomy can be provided on a patient-specific basis. The surgical kit can include a patient-specific alignment guide and, optionally, a patient-specific or an off-the-self fixation plate. For an open-wedge osteotomy, the surgical kit can include a patient-specific or an off-the-shelf implantable wedge. The patient-specific tools and implants are customized and prepared for the specific patient during a computer-assisted pre-operative planning stage in which the patient's anatomy is modeled in three dimensions from two-dimensional image scans. Patient-specific or customized blades can be included to provide adjustable depth control or automatic length. Other, non-customized blades can also be included.

Figure 22:
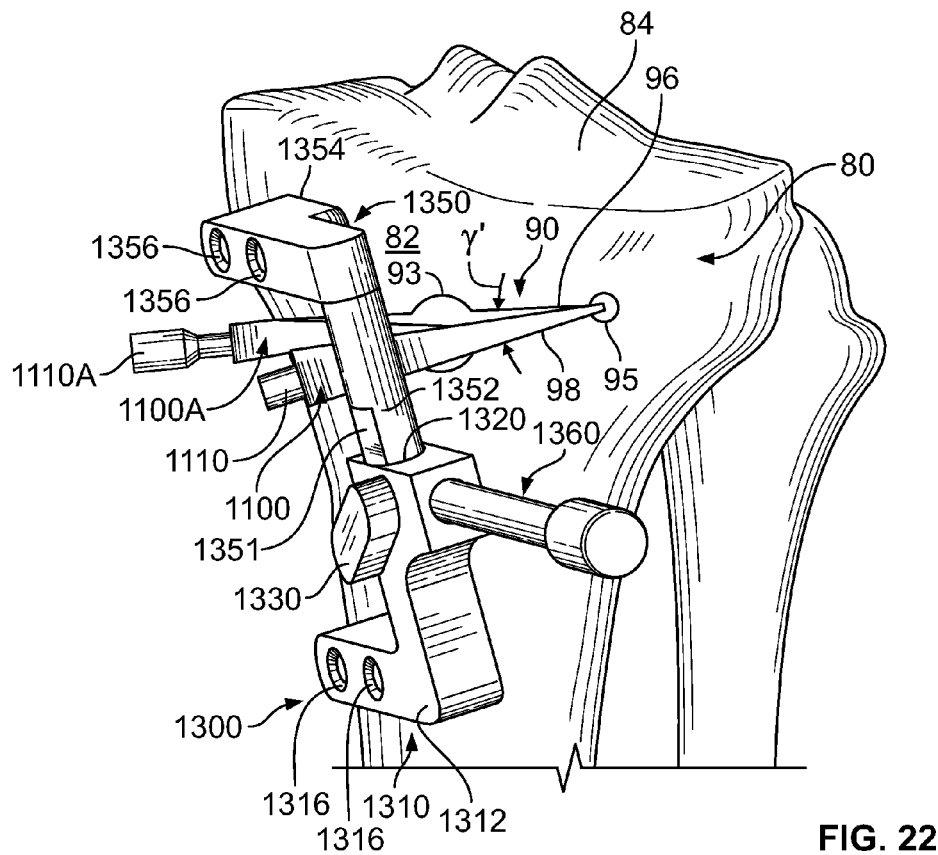
FIG. 22 is an environmental view of the osteotomy securing device of FIG. 20 shown with a spreader and an osteotome inserted in the osteotomy.
Figure 23:
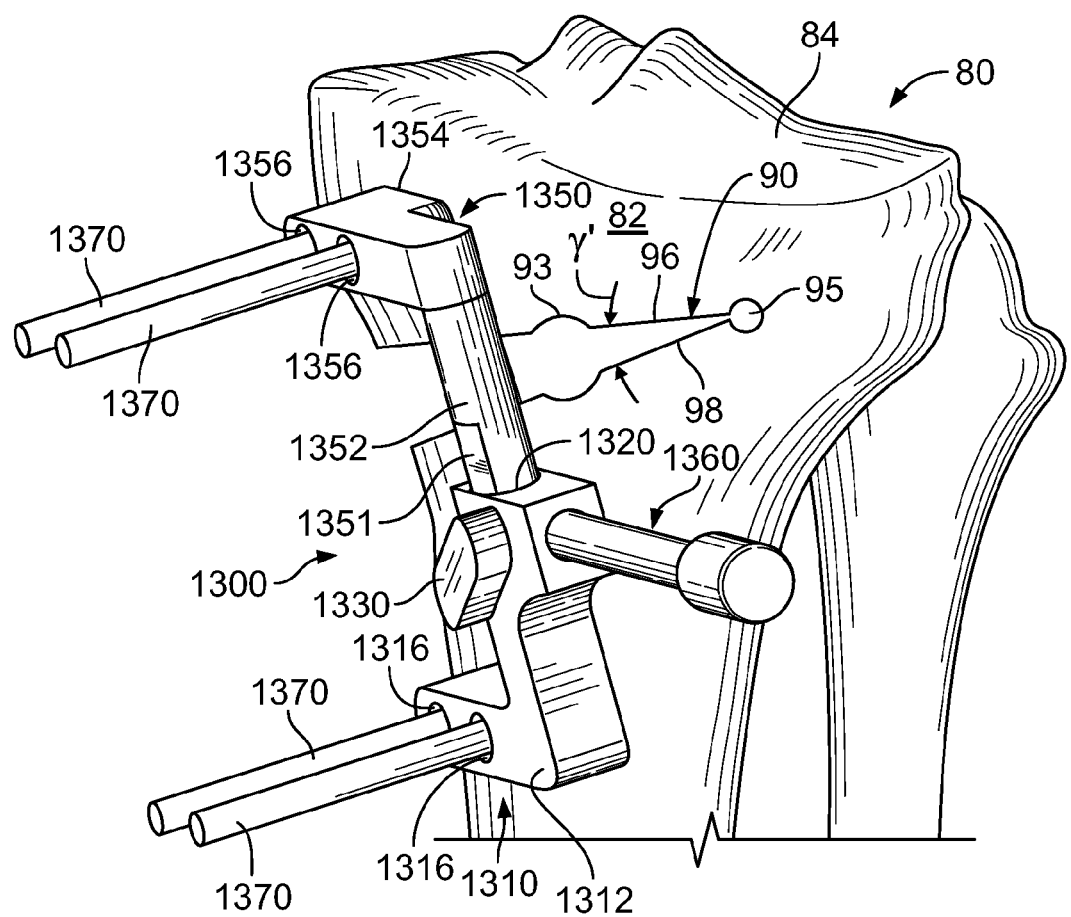
FIG. 23 is an environmental view of the osteotomy securing device of FIG. 20 holding the osteotomy open.
Figure 24:
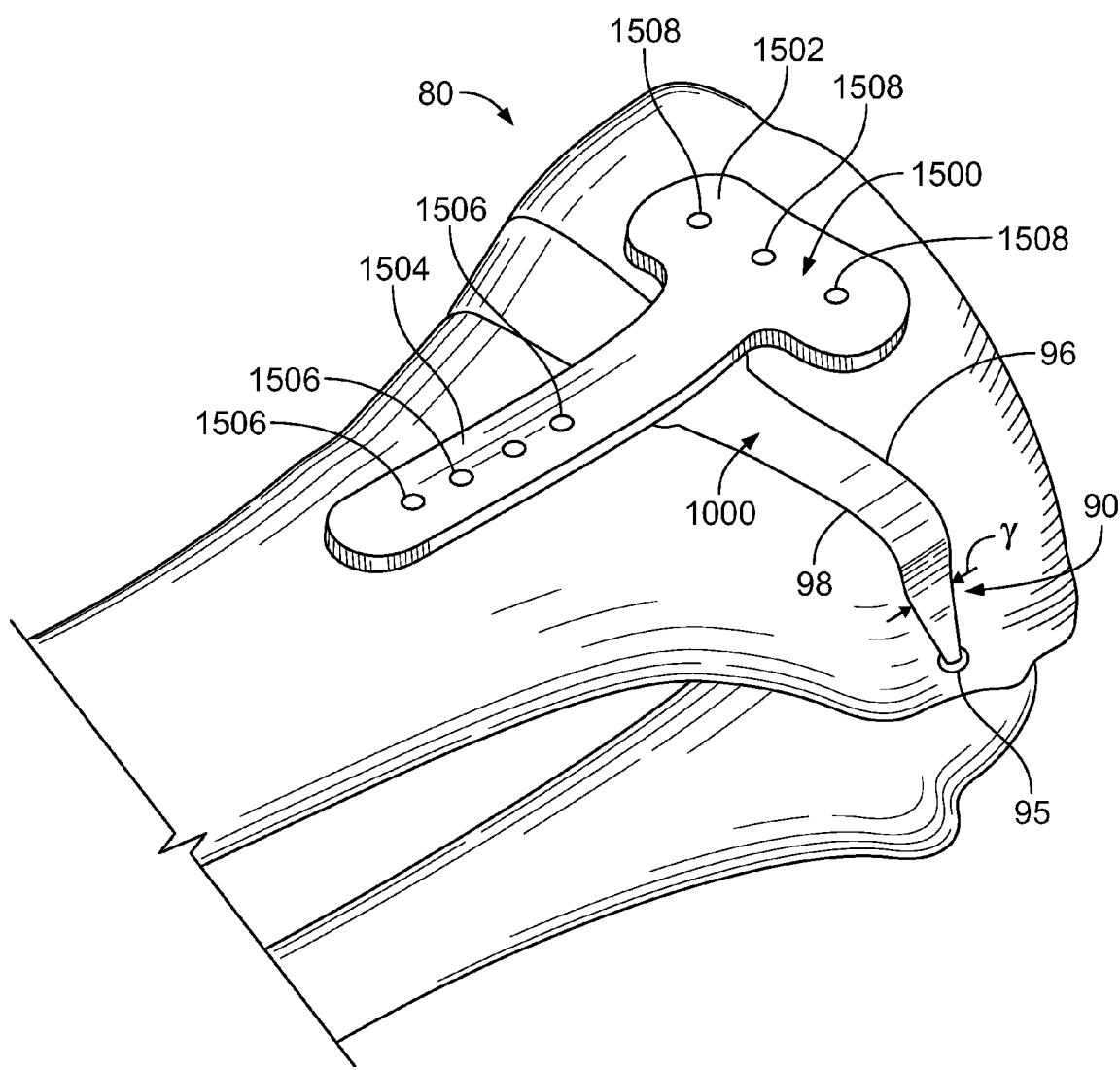
FIG. 24 is an environmental view of a patient-specific osteotomy implant and fixation plate.

Additional embodiments of patient-specific implants and instruments for performing open osteotomy are illustrated in FIGS. 15A-24. The instruments include a patient-specific resection/drill alignment guide (or osteotomy guide, for short) 900, a drill guide 920 (FIGS. 15A and 15B), patient-specific osteotomy implants 1000 and 1000A (FIGS. 16A-16C), a patient-specific osteotomy spreader 1100 (FIG. 17), a graduated osteotome 1100A (FIG. 21), an impactor assembly 1200 (FIG. 18), an osteotomy securing device 1300 (FIG. 20) and a fixation plate 1500 (FIG. 24). These instruments and implants can also be used to supplement and/or replace corresponding instruments and implants discussed above in connection with FIGS. 1-14B and can also be included in the surgical kit described above for a particular patient and surgeon as optional additional or interchangeable components.

Generally, medical scans of the patient's anatomy, including the proximal femur and tibia, are imported into a computer program, such as the software commercially available from Materialise USA, as discussed above. A virtual three-dimensional model of the patient's anatomy is reconstructed using the software. A surgeon's planned osteotomy, including osteotomy angle correction and extent can be virtually modeled and patient-specific guides and other instruments can be designed based on the virtual model. More specifically, the osteotomy guide 900 shown in FIGS. 15A and 15B, the osteotomy implants 1000 and 1000A shown in FIGS. 16A-16C and the osteotomy spreader 1100 shown in FIG. 17 can all be patient-specific and designed from the medical scans of the patient. The fixation plate 1500 can also be patient-specific, although a non-custom fixation plate can also be used. Before describing in further detail the various instruments and implants referenced above in connection with FIGS. 15A to 24, an exemplary procedure using these instruments and implants is described below.

Figure 15A:
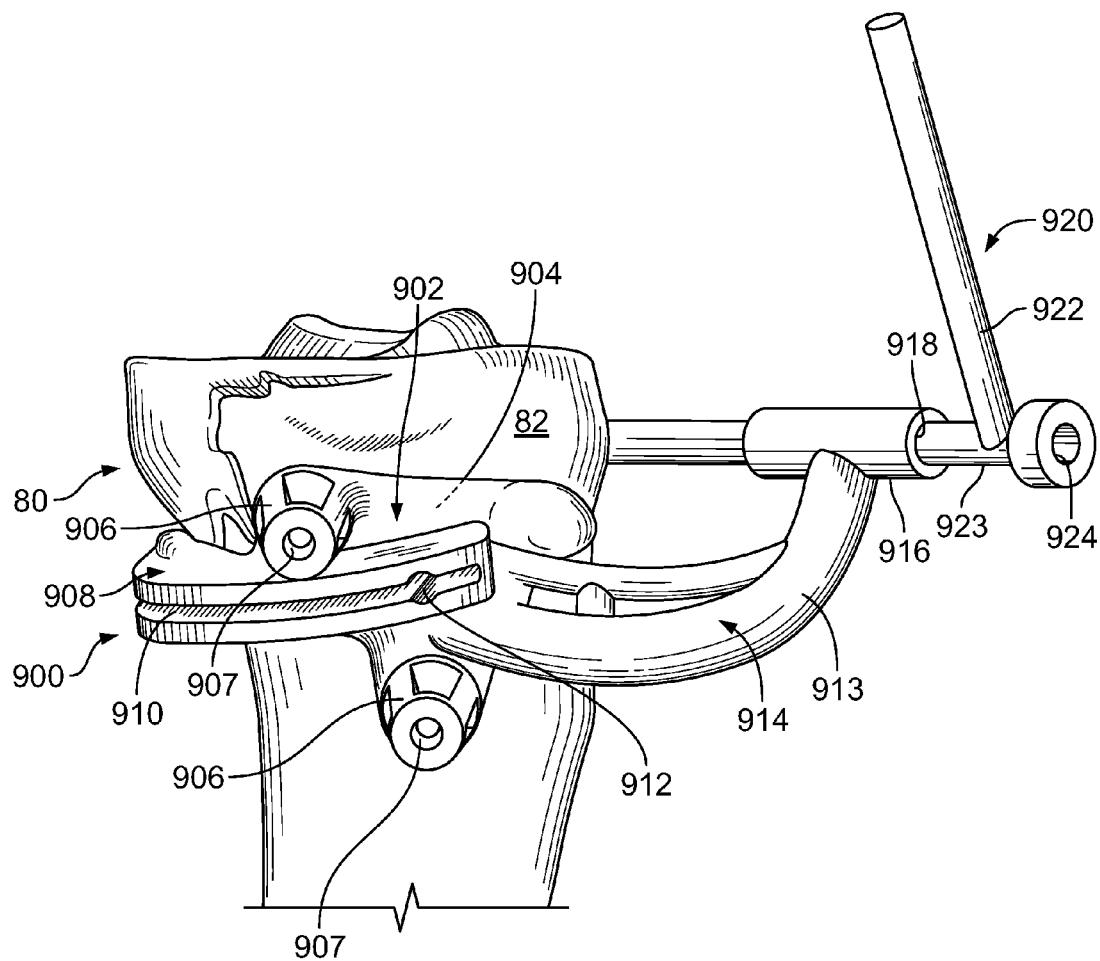
FIGS. 15A and 15B are environmental views of a patient-specific resection/drill alignment guide for tibial osteotomy according to the present teachings.
Figure 19A:
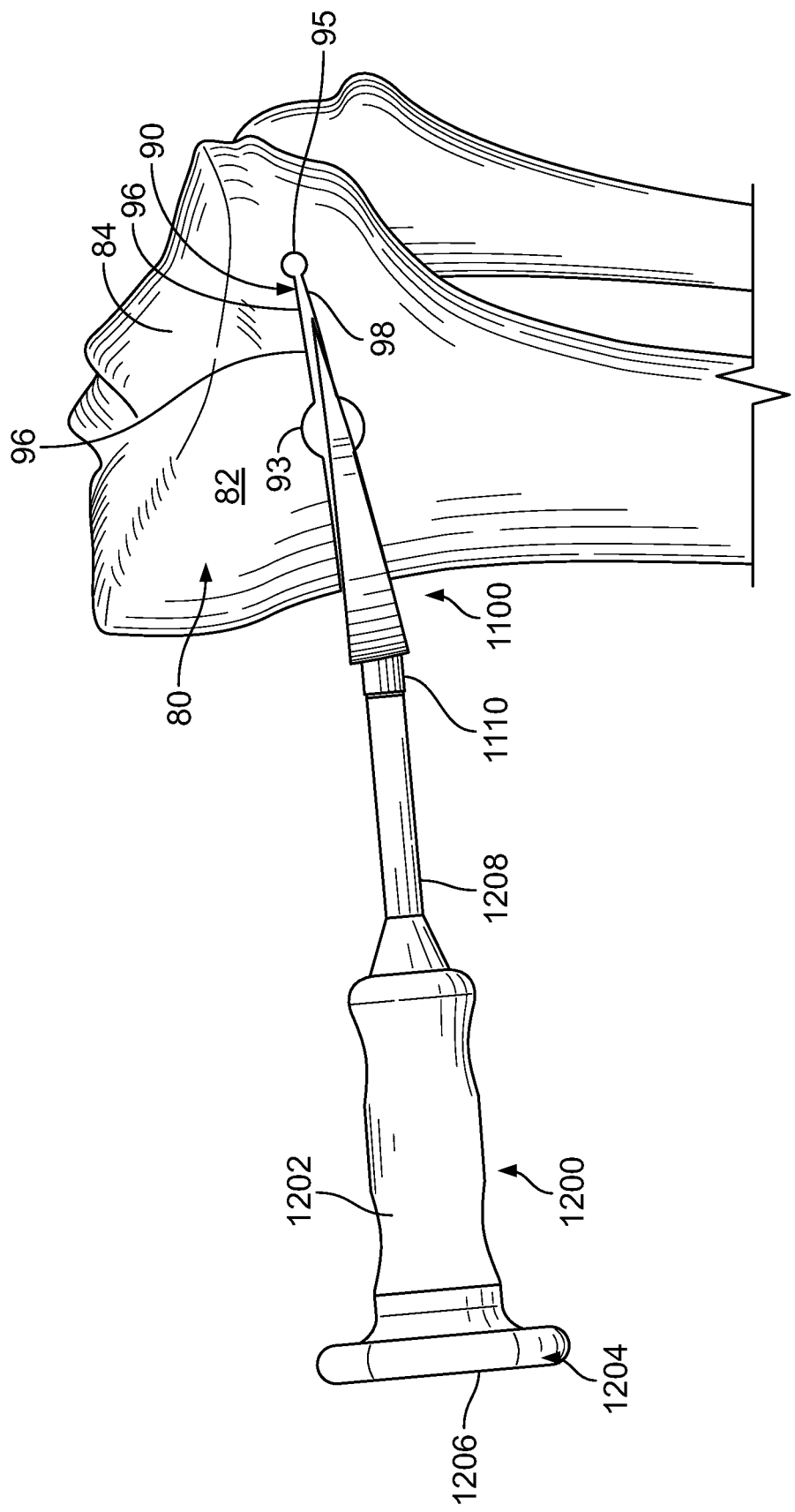
FIG. 19A is an environmental perspective view illustrating opening an osteotomy with a patient-specific osteotomy spreader according to the present teachings.

Referring to FIG. 15A, the osteotomy guide 900 is mounted or nested in a unique (only one) position on a surface 82 of the tibia 80 according to the preoperative plan for the patient for performing an osteotomy to correct the patient's joint misalignment or other defect. Referring to FIG. 19A, a patient-specific osteotomy spreader 1100 is driven into the osteotomy 90 that has been previously cut using the osteotomy guide 900. The osteotomy 90 can be optionally opened further to allow for the insertion of the osteotomy implant 1000 or 1000A using the graduated osteotome 1100A of FIG. 21. The osteotomy securing device 1300 can be affixed across the osteotomy 90 to keep the osteotomy 90 open. The osteotomy spreader 1100 and the graduated osteotome 1100A, if used, can then be removed, as shown in FIGS. 22 and 23. The patient-specific osteotomy implant 1000 (or 1000A) can be implanted into the opened osteotomy 90 and a fixation plate 1500 can be affixed over the osteotomy 90 and the osteotomy implant 1000 (1000A), as shown in FIG. 24. These implants, instruments and procedures are described in further detail below.

Figure 15B:
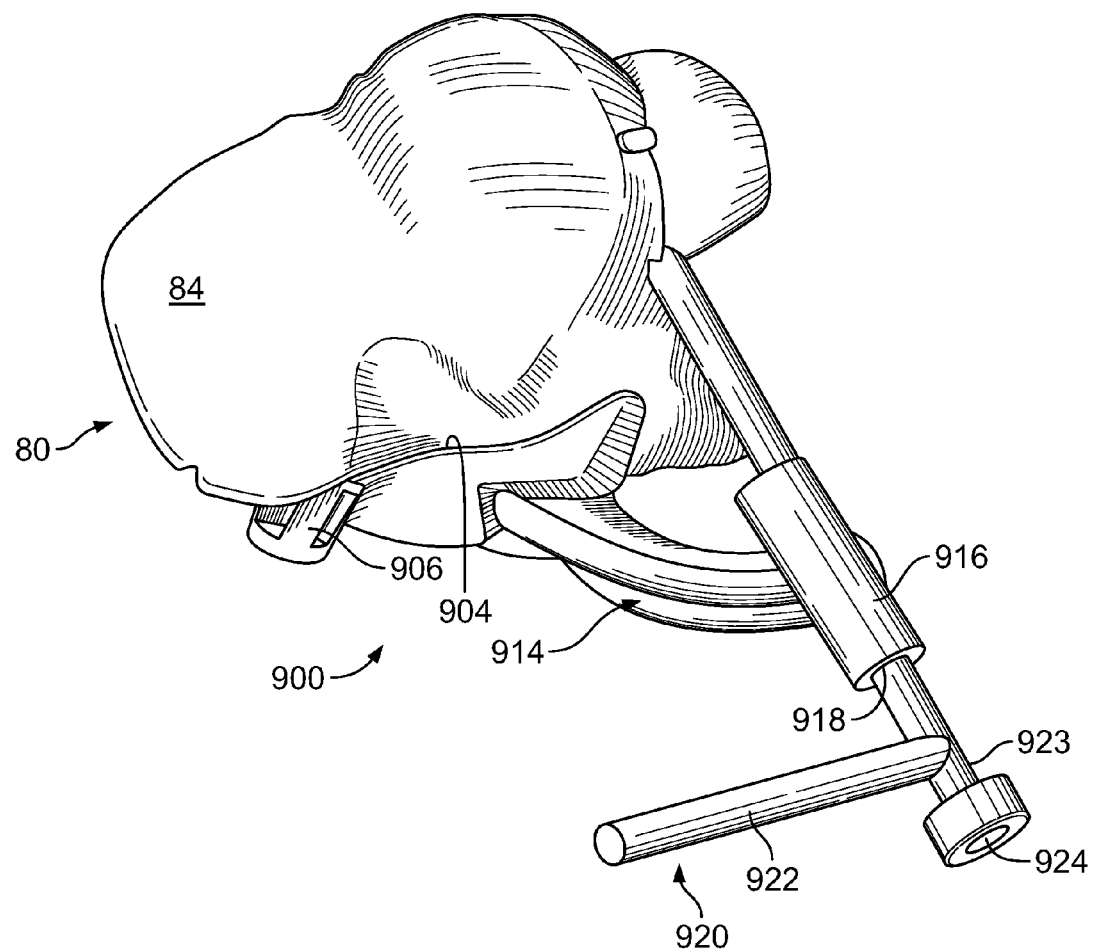

Referring to FIGS. 15A and 15B, the osteotomy guide 900 includes an alignment portion 902, a resection (and drill) portion 908 for guiding a resection and drilling a hole through the alignment portion 902, a drill support 914 and a drill guide 920. The alignment portion 902, the resection portion 908 and the drill support 914 can be made as a one-piece integral (monolithic) unit. The drill guide 920 can be removably coupled to the drill support 914, as discussed below. The alignment portion 902 includes a patient-specific three-dimensional inner surface 904 that is designed and configured during the preoperative plan to be complementary and nestingly mate with a corresponding outer surface 82 (including patient-specific natural bone landmarks thereon, such as osteophytes, for example) of the patient's tibia 80 only in one position. The alignment portion 902 can also include two or more guiding formations 906 having through bores 907 for attaching the osteotomy guide 900 to the tibia 80 using K-wires, pins or other bone fasteners. Two guiding formations 906 are illustrated in FIG. 15A.

With continued reference to FIG. 15A, the resection portion 908 can include a resection slot 910 for guiding a cutting tool to perform the osteotomy 90 according to the preoperative plan for the patient. The resection slot 910 passes through the alignment portion 902 and is sized and oriented relative to the alignment portion 902 (and therefore relative to the tibia 80) according to preoperative patient-specific, surgeon-approved, selected anatomic considerations, and other considerations. In some embodiments, the resection portion 908 can include a unicortical or a longer bicortical 912 intersecting the resection slot 910 and configured for guiding the insertion of the osteotomy implants 1000, 1000A, as discussed below and drilled before initiating the resection procedure through the resection slot 910. A unicortical hole 912 is a blind hole that stops short of penetrating the cortical bone on the opposite side of the resection, while a bicortical hole 912 is a through hole, i.e., a hole long enough to penetrate the opposite side of the cortical bone. The drill hole 912 is illustrated in FIG. 15A. A corresponding pre-resection guiding bone hole, such as the bone hole 93 described above in the embodiments related to FIG. 11, is drilled through the drill hole 912 into the tibia 80 for guiding the implant.

With continued reference to FIG. 15A, the drill support 914 can include a curved rig or frame or other three-dimensional structure 913 extending from the alignment portion 902 having a guiding tube 916 with a through bore 918. The drill support 914 is sized and shaped such that the through bore 918 can orient the drill guide 920 to drill a stress-relief hole 95 at the sharp edge (end) of the osteotomy 90, as shown in FIG. 19A. The drill guide 920 can include a tubular shaft 923 that is removably inserted through the guide tube 916 and has a longitudinal opening 924 for stabilizing and guiding a drill bit to drill the stress-relief hole 95 along the edge of the osteotomy 90. The stress-relief hole 95 reduces crack initiation by rounding the sharp edge of the osteotomy 90 and reducing stress concentration. The drill guide 900 can also include a handle 922 for holding and stabilizing the drill guide 920 during use.

Figure 25:
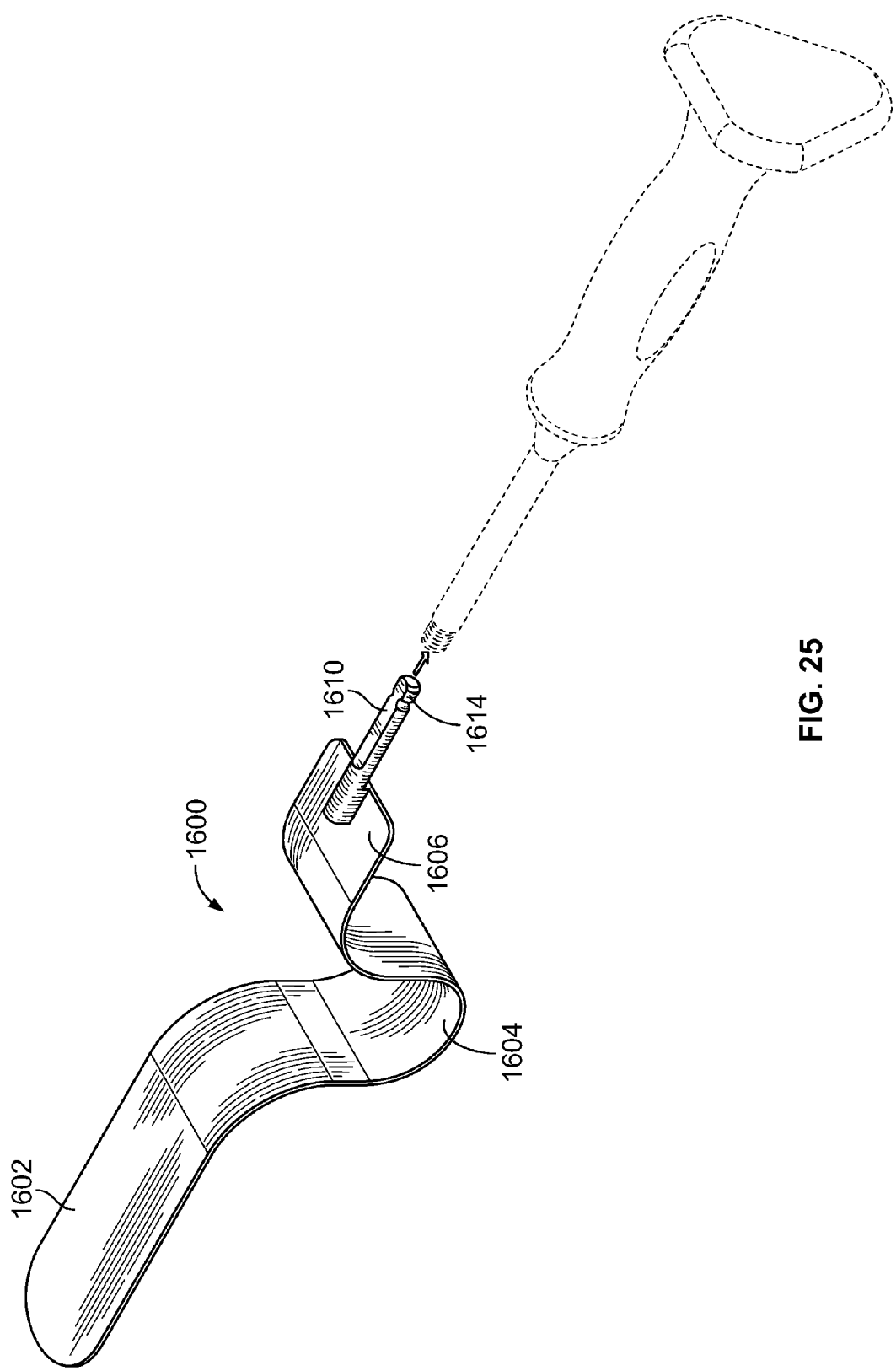
FIG. 25 is a perspective view of a posterior blade guard according to the present teachings.
Figure 26:
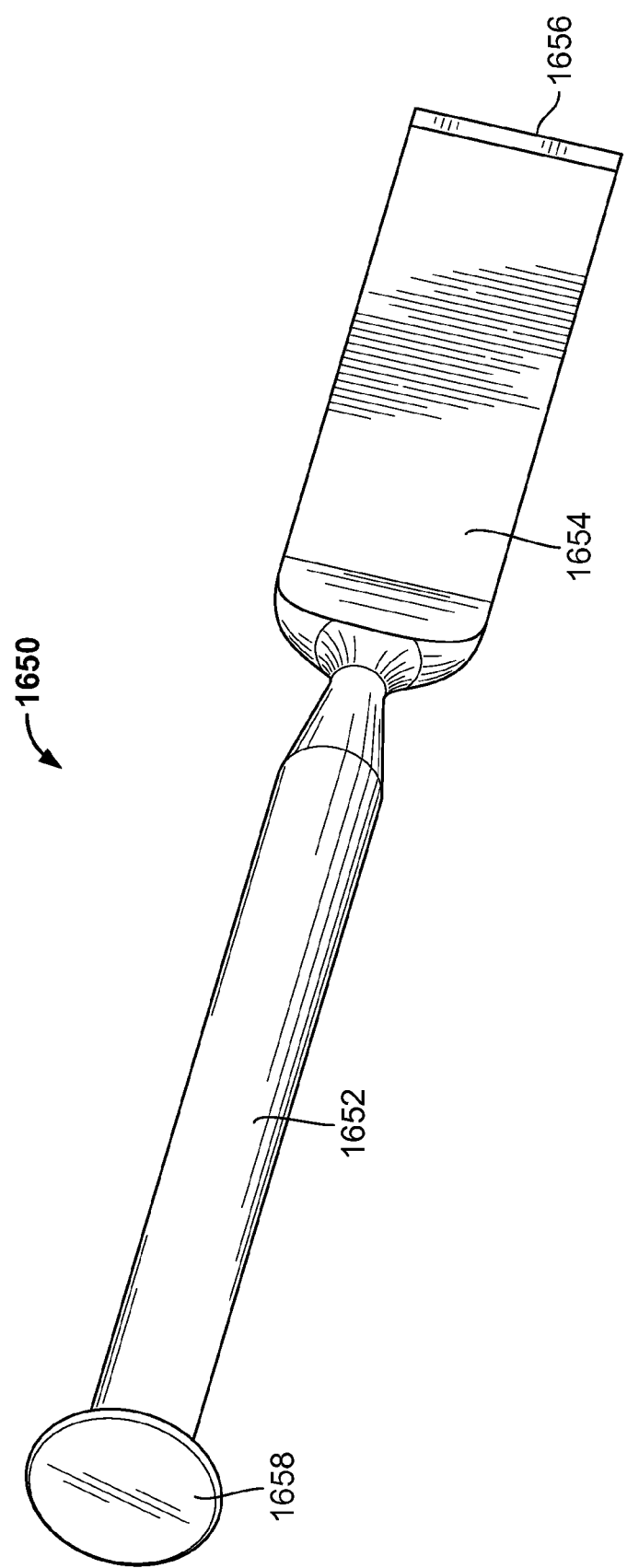
FIG. 26 is an auxiliary osteotome according to the present teachings.

In some embodiments, before performing the osteotomy 90 through the resection slot 910 and before drilling the guiding hole 93 through the drill hole 912 of the osteotomy guide 900, a posterior blade guard 1600, shown in FIG. 25, can be used to protect nerve bundles and or other soft tissue in the posterior surface of the knee. The posterior blade guard 1600 has a thin, three-dimensionally ribbon-like body that includes a flat (substantially planar) distal portion 1602, a curved U-shape portion 1604, and a flat proximal portion 1606 from which a connector shaft 1610 extends. Intraoperatively, the distal portion 1602 is inserted against the posterior surface of the tibia 80 and functions as a blade stop to protect posterior nerve bundles, ligaments and other tissue from being inadvertently damaged during the osteotomy. The middle portion 1604 functions as a retractor of soft tissue about the incision for the procedure. The shaft 1610 can have an end portion 1614 configured for coupling with an osteotomy handle, such as, for example, the tip 1210 of the impactor assembly 1200. After resection using the osteotomy guide 900, an auxiliary osteotome 1650, shown in FIG. 26, can be used to finish the osteotomy 90, if not fully completed. The auxiliary osteotome 1650 includes a handle or shaft 1652 carrying a distal blade 1654 with a sharp distal edge 1656 and a proximal impactor surface 1658. The posterior blade guard 1600 and the auxiliary osteotome 1650 can also be included in the osteotomy kit.

Figures 16A, 16B:
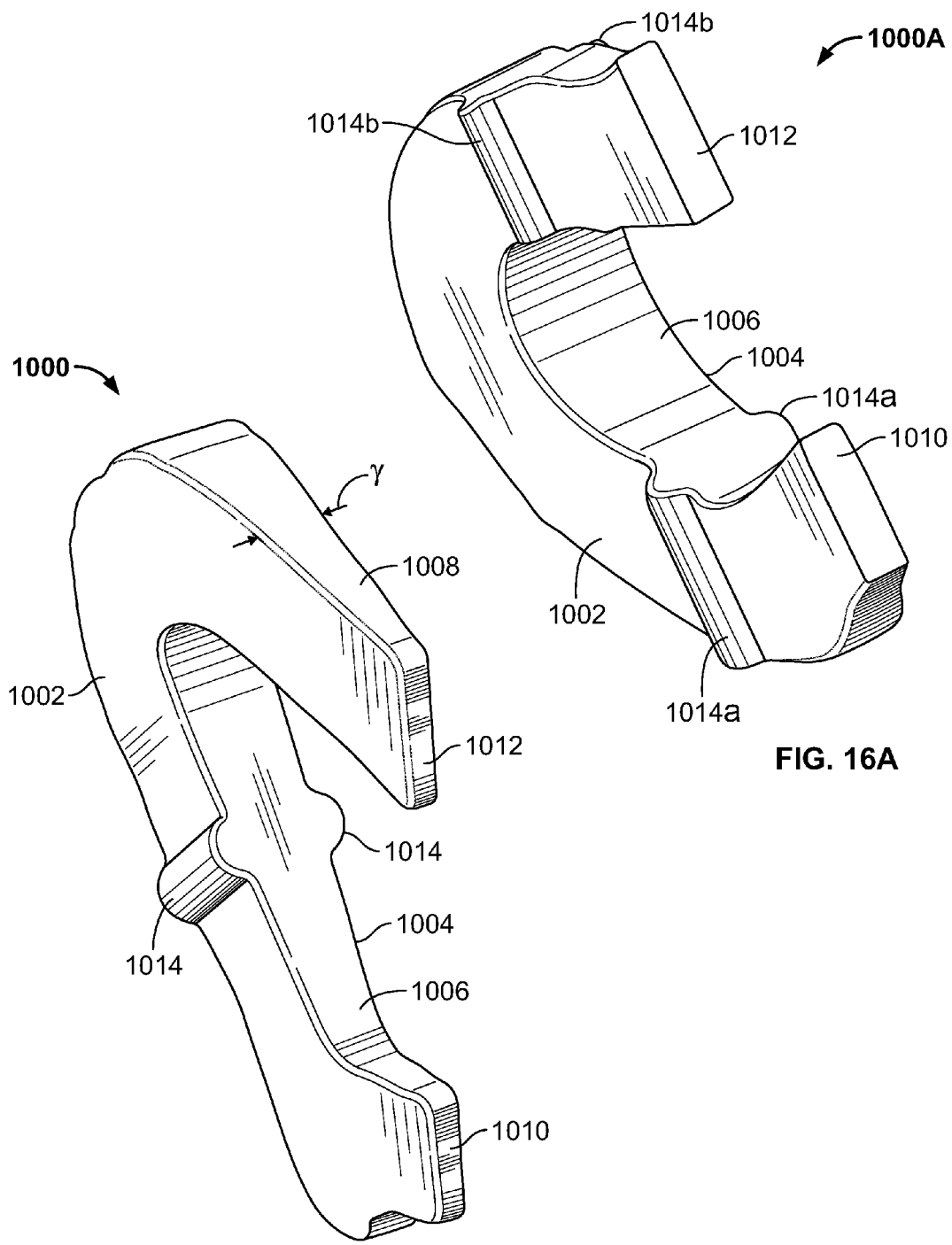
FIG. 16A is a perspective view of an exemplary patient-specific osteotomy implant according to the present teachings.
FIGS. 16B and 16C are perspective views of another patient-specific osteotomy implant according to the present teachings.
Figure 16C:
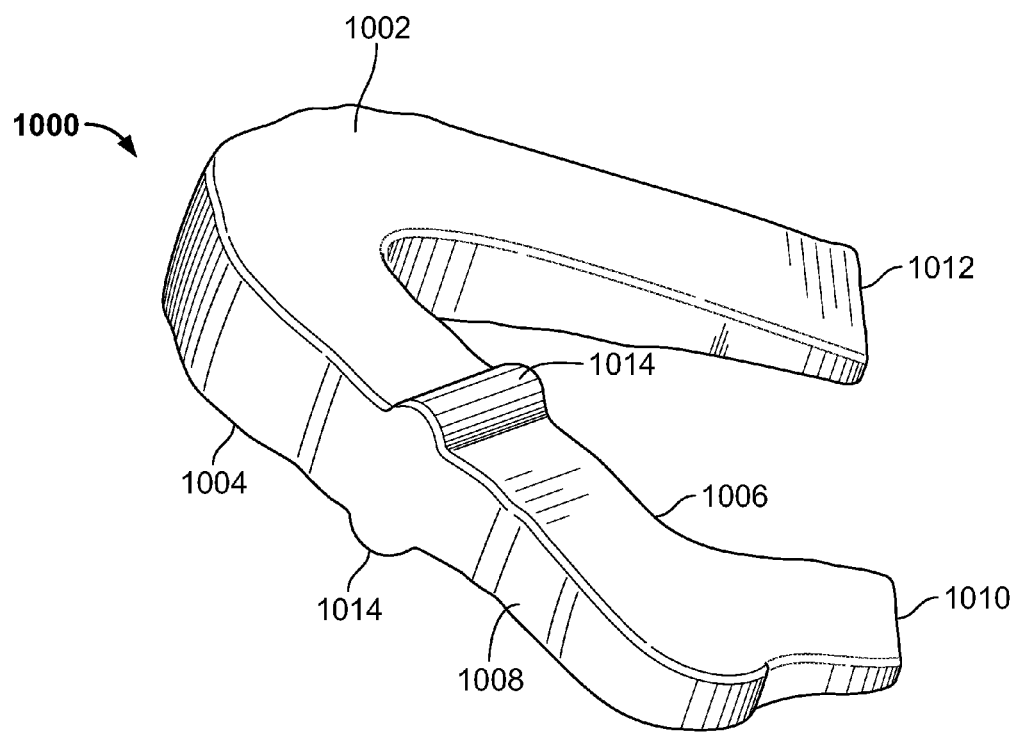
Figure 17:
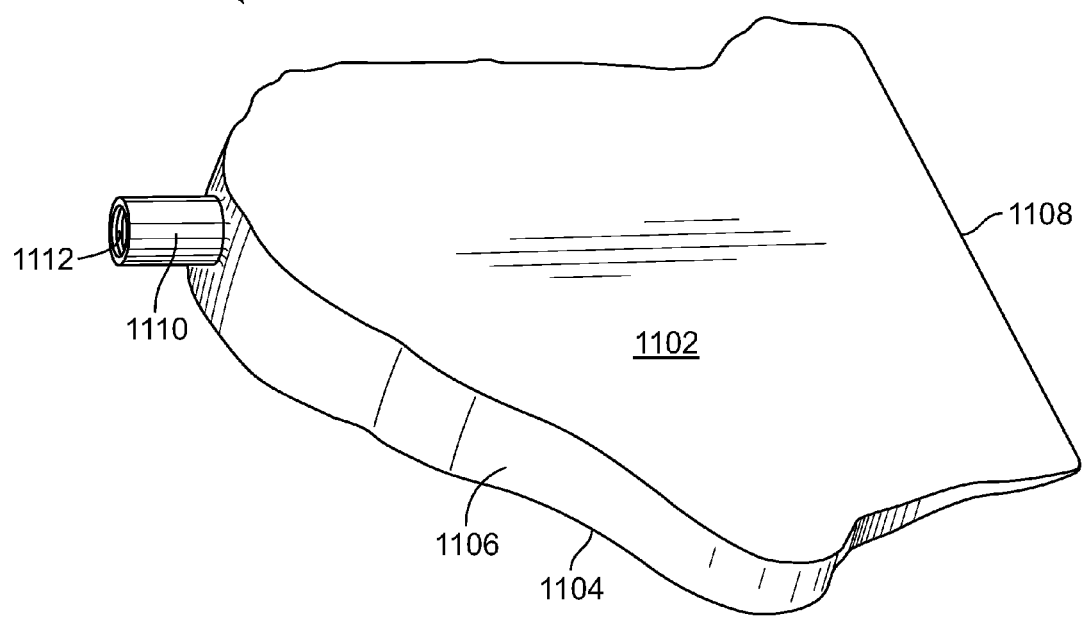
FIG. 17 is a perspective view of a patient-specific osteotomy spreader according to the present teachings.
Figure 18:
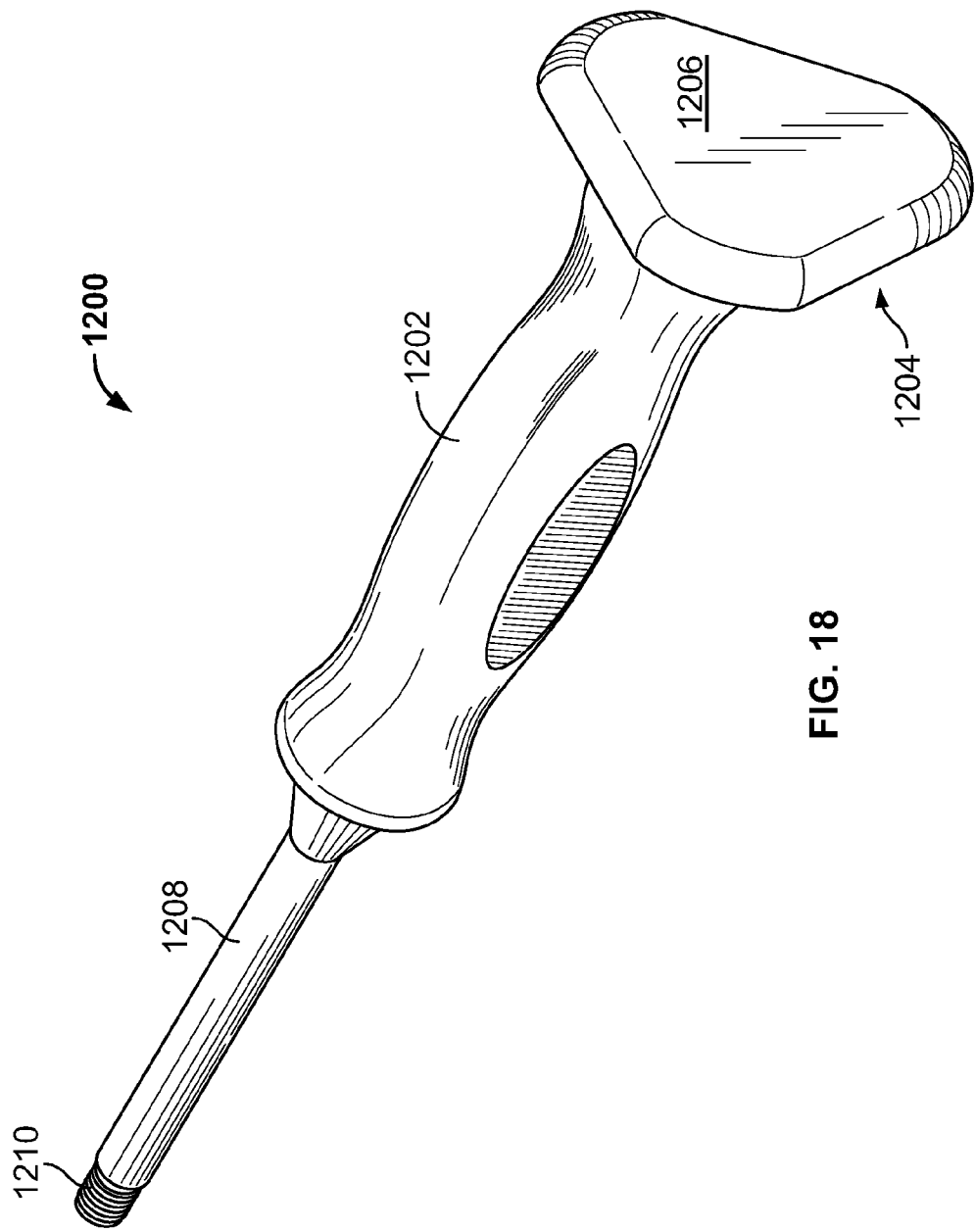
FIG. 18 is a perspective view of an impactor assembly according to the present teachings.

Referring to FIGS. 16A-16C, exemplary embodiments of an osteotomy implant 1000 and 1000A are illustrated. The osteotomy implant 1000 is configured for a procedure using a unicortical drill hole 912 and includes a corresponding curved hump or protrusion or curved ridge 1014, as shown in FIGS. 16B and 16C. The curved ridge 1014 is configured to be received into the osteotomy hole 93 drilled through the drill hole 912 of the osteotomy guide of FIG. 15A. The osteotomy implant 1000A is configured for a procedure using a deeper, bicortical hole 912 and includes two corresponding protrusions or curved ridges 1014a, 1014b, as shown in FIG. 16A. The curved ridge 1014 or ridges 1014a, 1014b can help align and direct the osteotomy implant 1000 (100A) into the bone along an insertion axis coinciding with the longitudinal axis of the curved ridge 1014 (or common longitudinal axes of curved ridges 1014a, 1014b). In the osteotomy implant 1000A, the insertion orientation is along an anterior-posterior orientation. Other orientations for inserting the osteotomy implant 1000 can also be selected by changing the location and orientation of the curved ridge 1014, such as, for example, along a medial to lateral direction or from an anterior-medial position toward a posterior-media position, as illustrated by the different orientations of the curved ridge 1014 in FIGS. 16B and 16C. In other respects, the osteotomy implants 1000, 1000A are similar and same reference numbers are used to describe similar or common to features. The osteotomy implant 1000 or 1000A is wedge-shaped and also U-shaped or horseshoe-shaped. Specifically, the osteotomy implant 1000 (1000A) includes first and second surfaces 1002, 1004 forming a wedge with wedge angle equal to a patient-specific osteotomy angle γ designed to be received in the osteotomy 90 to correct the patient's joint misalignment, as determined during the preoperative plan.

The osteotomy implant 1000 (1000A) can have a horseshoe shape or a U shape or other open-channel shape that is formed by a peripheral surface between the first and second surfaces 1002, 1004 of the osteotomy implant 1000 (1000A). The peripheral surface includes an outer wall surface 1008, an inner wall surface 1006 and first and second end surfaces 1010, 1012. The inner wall surface 1006 defines an opening for allowing access to a stem or other component of a tibial implant, if a tibial implant is to be implanted at some later time. The outer wall surface 1008 is configured during the preoperative plan to match and be continuous with the outer surface of the tibia of the patient adjacent to the osteotomy 90. The first and second end surfaces 1010, 1012 are generally rounded or not sharp and are designed to end before the stress-relief hole 95.

As discussed above in connection with osteotomy implants 400, 700, the osteotomy implants 1000, 100 can be made of various biocompatible materials including, for example, various solid metals or alloys, solid PEEK, porous metal and porous metal alloys, porous thermoplastics, such as PEEK (polyether ether ketone), PEKK (polyether ketone ketone), osteoinductive or osteoconductive materials, including Pro Osteon®, commercially available from Biomet, Inc., Warsaw, Ind., with or without a resorbable filler material, and/or combinations thereof. In some embodiments, two or more different materials can be used in each implant 1000 (1000A). For example, the central curved portion of the implant 1000 (100A) can be made of a porous material (porous metal, porous PEEK or PEKK), while portions around and including the protrusions 1014, or 1014a, 1014b, as well and portions adjacent and including first and second end surfaces 10110, 1012 can be made of a solid material (solid metal, solid PEEK or PEKK).

Referring to FIGS. 17, 18, 19A, 19B and 21, after the osteotomy 90 is cut into the tibia 80 using the osteotomy guide 900 of FIG. 15A, the patient-specific osteotomy spreader 1100 can be used to open up the osteotomy 90 in preparation for receiving an osteotomy implant 1000 (1000A). The osteotomy spreader 1100 is wedge-shaped. The wedge is defined by first and second opposing surfaces 1102, 1104 intersecting at a sharp edge 1108 and forming an angle equal to the patient-specific angle γ of the osteotomy implant 1000 (1000A). The osteotomy spreader 1100 includes a peripheral surface 1106 which can also be designed during the preoperative plan to be patient-specific. The osteotomy spreader 1100 can also be used as a trial for the osteotomy implant 1000 (1000A). The osteotomy spreader 1100 can include a short tubular shaft 1110 with internal threads 1112 for connecting to an externally threaded tip 1210 of the impactor assembly 1200, shown in FIG. 18. In some embodiments, the external and internal threads in the osteotomy spreader 1100 and the threaded tip 1210 may be reversed. In other embodiments, the osteotomy spreader 1100 and the impactor assembly can be coupled by other connecting means, such as bayonet coupling, taper to taper connection, or other quick connect/disconnect couplings.

Figure 19B:
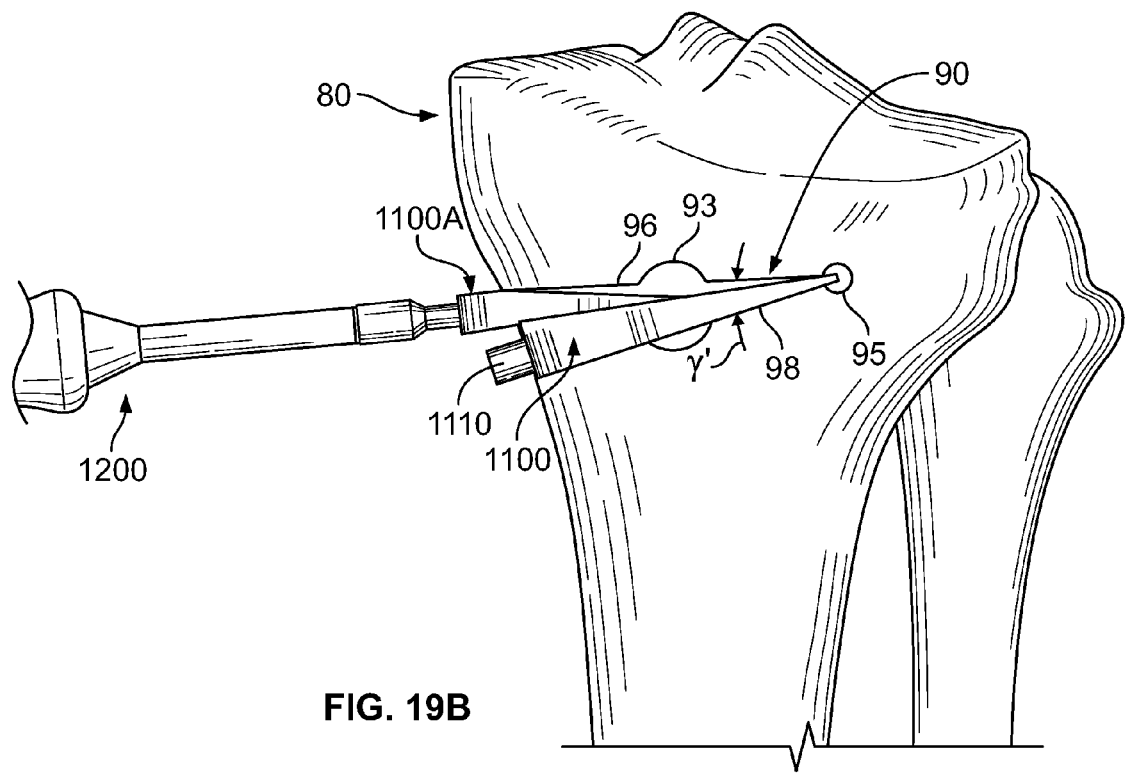
FIG. 19B is an environmental perspective view illustrating further opening the osteotomy of FIG. 19A with a graduated osteotome according to the present teachings.

The impactor assembly 1200 includes an impactor plate 1204 having an impactor surface 1206, a handle 1202 coupled to the impactor plate 1204, and a shaft 1208 extending from the handle 1202 and terminating at the externally threaded tip 1210. The impactor assembly 1200 can be coupled to the osteotomy spreader 1100, which is then pushed against the osteotomy 90. Striking the impactor surface 1206 with a mallet opens the osteotomy 90, as shown in FIG. 19A. When the osteotomy spreader 1100 is fully driven into the osteotomy 90, the opposite faces 96, 98 of the osteotomy 90 form the predefined osteotomy angle γ. To allow for ease in the implantation of the osteotomy implant 1000 (1000A), the osteotomy 90 is further opened by an additional small amount, as shown in FIG. 19B. The impactor assembly 1200 is removed from the osteotomy spreader 1100 and is attached to the osteotome 1100A. The osteotome 1100A includes a tubular shaft 1110A with internal threads 1112A for threadably engaging the threaded tip 1210 of the shaft 1208 of the impactor assembly 1200. In some embodiments, the external and internal threads in the osteotome 1100A and the threaded tip 1210 may be reversed. Alternative, other types of connections can be used, such as bayonet coupling, taper to taper connection, or other quick connect/disconnect couplings.

The osteotome 1100A includes first and second surfaces 1102A, 1104A forming a wedge having a peripheral wall surface 1106A and a sharp edge 1108A. The osteotome 1100A includes a plurality of engraved or otherwise marked lines or gradation markings 1120 on the first surface 1102A corresponding to additional amount of osteotomy opening. The proximal end portion 1105A of the first surface 1102A can be parallel (not inclined relative) to the second surface 1104A, so that the proximal end portion 1105A can also serve as a stop for the osteotome 1100A.

Referring to FIGS. 19A and 20-23, the osteotome 1100A, coupled to the impactor assembly 1200, is stacked over the osteotomy spreader 1100 and driven into the osteotomy 90 up to a predetermined gradation marking 1120 to open up the osteotomy by an insertion angle γ' slightly larger than the osteotomy angle γ. The opposite faces 96, 98 of the osteotomy 90 are secured at the insertion angle γ' using the osteotomy securing device 1300, as shown in FIG. 22. The osteotomy securing device 1300 can be an adjustable offset tie rod structure that includes first and second members 1310, 1350. The first member 1310 includes first and second portions 1302, 1313 forming an L-shape. A block 1304 extends from the second portion 1313 and has a bone engagement surface 1314, shown in FIG. 20. One or more holes 1316 extend from an outer surface 1312 of the second portion 1313 to the bone engagement surface 1314 of the block 1304 of the first member 1310 for attaching the first member 1310 to the tibia 80 on a side of the osteotomy 90 adjacent to face 98 with pins or other bone fasteners 1370, as shown in FIG. 23. The first portion 1302 of the first member 1310 has an elongated cylindrical bore 1320 for adjustably coupling the first member 1310 to the second member 1350. The osteotomy securing device 1300 can also include an elongated handle 1360 for stabilizing the osteotomy securing device 1300 during attachment to the tibia 80. In some embodiments, the handle 1360 can be a shaft extending from the first member 1310 of the osteotomy securing device 1300.

Figure 20:
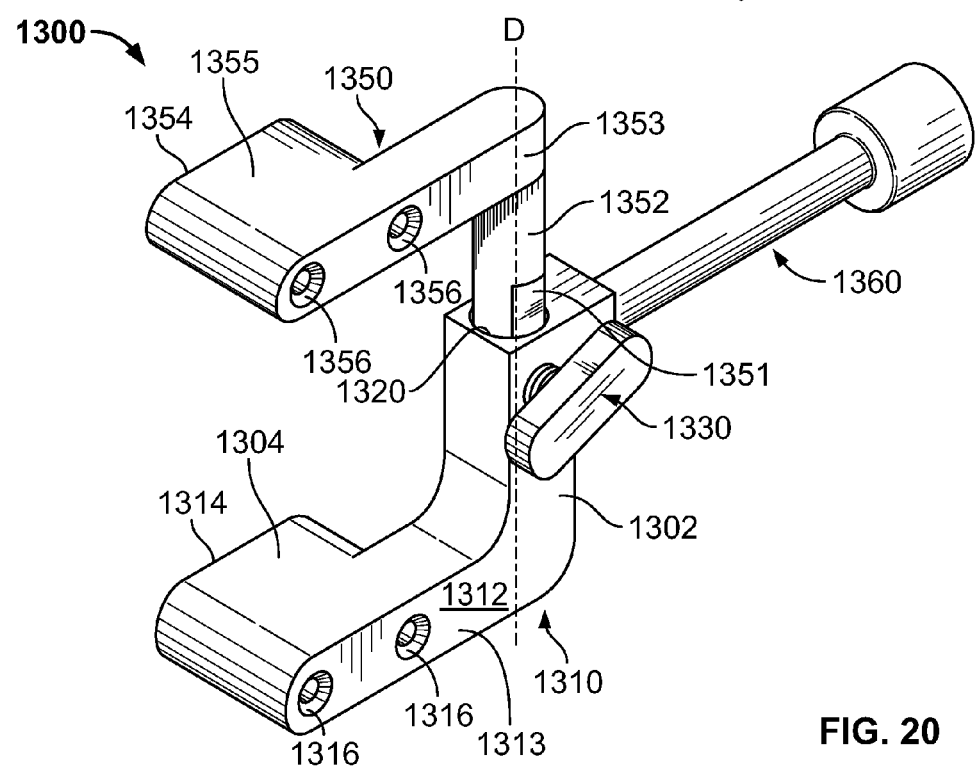
FIG. 20 is a perspective view of an osteotomy securing device according to the present teachings.
Figure 21:
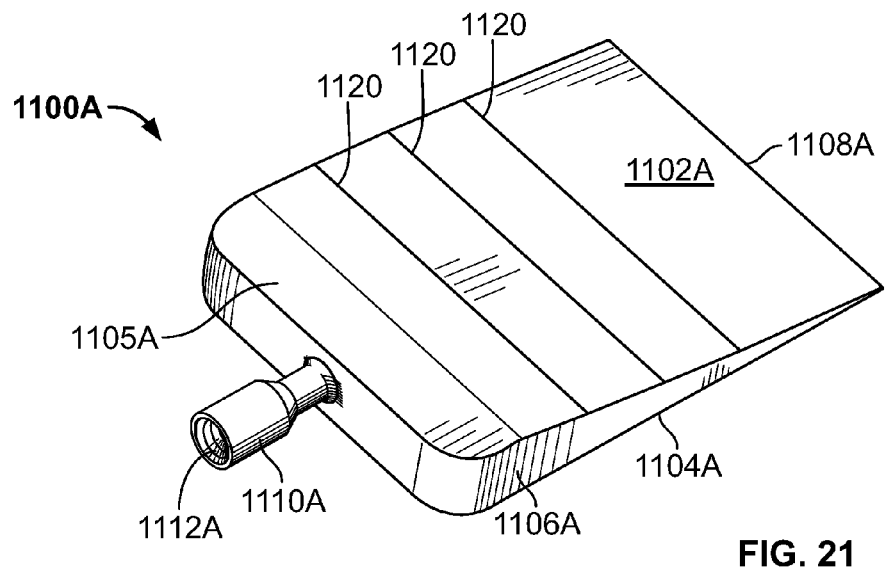
FIG. 21 is a perspective view of an osteotome according to the present teachings.

With continued reference to FIGS. 19A and 20-23, the second member 1350 includes first and second portions 1352, 1353 forming an L-shape. A block 1355 extends from the second portion 1353 and has a bone engagement surface 1354. One or more holes 1356 extend through the second portion 1353 and the block 1355 of the second member 1350 for attaching the second member 1350 to the tibia 80 on a side of the osteotomy 90 adjacent to face 96 with pins or other bone fasteners 1370, as shown in FIG. 23. The first portion 1352 of the second member 1310 can be an elongated cylindrical shaft (1352) with a flat or planar cutout surface 1351. The cylindrical shaft 1352 is slidably received into the cylindrical bore 1320 of the first member 1310 and is adjustably coupled to the first member 1310 along an axis D, such that the osteotomy securing device 1300 can span the opened osteotomy 90, as shown in FIG. 22. The osteotomy securing device 1300 can include a wing nut, set screw or other locking member 1330 for locking and securing the relative position of the first and second member 1310, 1350 relative to one another to maintain the osteotomy opening at the insertion angle γ', as shown in FIG. 22. The locking member 1330 can include a portion that threadably passes through the first portion 1302 and through the cylindrical bore 1320 of the first member 1310, presses against the planar surface 1351 of the cylindrical shaft 1352 and prevents sliding of the cylindrical shaft 1352 relative to the cylindrical bore 1320 when the locking member 1330 is threadably tightened, as shown in FIG. 20.

Referring to FIGS. 22-24, after the implant insertion angle γ' is stabilized with the osteotomy securing device 1300, as discussed above, the osteotome 1100A and the osteotomy spreader 1000 can be removed, and the osteotomy implant 1000 (1000A) inserted into the osteotomy opening formed by the insertion angle γ'. After full insertion and implantation, the osteotomy securing device 1300 is removed and the first and second faces 96, 98 of the osteotomy 90 are brought into contact with the osteotomy implant 1000 (1000A) at the predetermined osteotomy angle γ (which is smaller than the implant insertion angle γ', as discussed above).

The osteotomy implant 1000 (1000A) and the osteotomy correction can be further secured using the fixation plate/implant 1500. As discussed above, the fixation plate 1500 can be either patient-specific, i.e., configured during the preoperative plan to have a patient-specific inner surface that mates with a corresponding surface of the patient's tibia after implantation of the osteotomy implant 1000 (1000A), or a non-custom fixation plate. In the illustration of FIG. 24, the fixation plate 1500 includes first and second portions 1502, 1504 configured in a T-shape and having corresponding fixation holes 1508, 1506 for bone screws. Another embodiment of a patient-specific fixation plate 400 is discussed above in connection with FIG. 3B and can be used instead of the fixation plate 1500.

As discussed above, various patient-specific alignment guides, resection guides, osteotomy guides, osteotomy implants, fixation plates and other osteotomy instruments can be used for correcting a joint misalignment. The various implants and instruments are not limited to the specific configurations and embodiments described above. It is contemplated that the various instruments and implants discussed above can be used interchangeably, such that a surgical kit for a specific patient and specific surgeon can include more that one set of implants and instruments to provide intraoperative choice between different or alternative surgical procedures for the same patient.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An osteotomy method comprising:
    attaching a patient-specific osteotomy guide to a corresponding surface of a tibia of a patient, the osteotomy guide having a three-dimensional engagement surface configured during a preoperative plan for the patient using computer imaging to mate as a negative surface of the corresponding surface of the tibia;
    drilling a guiding hole into the tibia through a drill hole of the osteotomy guide;
    making an osteotomy at a patient-specific orientation through a resection slot of the osteotomy guide, the resection slot intersecting the drill hole and configured for the specific patient during the preoperative plan of the patient;
    removing the osteotomy guide; and
    opening first and second faces of the osteotomy to form a first angle using a patient-specific osteotomy spreader.

2. The osteotomy method of claim 1, further comprising:
    attaching an adjustable osteotomy securing device to span the osteotomy; and
    securing the osteotomy at a second angle greater than the first angle.

3. The osteotomy method of claim 2, further comprising removing the osteotomy spreader; and
    implanting a patient-specific osteotomy implant into the osteotomy, the patient-specific osteotomy implant configured with a wedge angle equal to the first angle, the first angle preoperatively determined for correcting a joint misalignment of the patient.

4. An osteotomy method comprising:
    attaching a patient-specific osteotomy guide to a corresponding surface of a tibia of a patient, the osteotomy guide configured during a preoperative plan for the patient to mate only in one position on the corresponding surface of the tibia;
    drilling a guiding hole into the tibia through a drill hole of the osteotomy guide;
    making an osteotomy at a patient-specific orientation through a resection slot of the osteotomy guide, the resection slot intersecting the drill hole and configured for the specific patient during the preoperative plan of the patient;
    removing the osteotomy guide;
    opening first and second faces of the osteotomy to form a first angle using a patient-specific osteotomy spreader; and
    opening the osteotomy to form a second angle greater than the first angle using an osteotome stacked over the osteotomy spreader.

5. The osteotomy method of claim 4, further comprising:
    attaching an adjustable osteotomy securing device to span the osteotomy; and
    securing the osteotomy at the second angle.

6. The osteotomy method of claim 5, further comprising removing the osteotomy spreader and the osteotome; and
    implanting a patient-specific osteotomy implant into the osteotomy, the patient-specific osteotomy implant configured with a wedge angle equal to the first angle, the first angle preoperatively determined for correcting a joint misalignment of the patient.

7. The osteotomy method of claim 6, further comprising removing the osteotomy securing device.

8. The osteotomy method of claim 7, further comprising bringing the first and second faces of the osteotomy from the second angle to the first angle.

9. The osteotomy method of claim 8, further comprising attaching a fixation plate across the osteotomy.

10. The osteotomy method of claim 4, further comprising drilling a stress-relief hole along an end of the osteotomy guided by the osteotomy guide.

11. An osteotomy method comprising:
    attaching a patient-specific osteotomy guide to a corresponding surface of a tibia of a patient, the osteotomy guide configured during a preoperative plan for the patient to mate only in one position on the corresponding surface of the tibia;
    drilling a guiding hole into the tibia through a drill hole of the osteotomy guide
    making an osteotomy at a patient-specific orientation through a resection slot of the osteotomy guide, the resection slot intersecting the drill hole and configured for the specific patient during the preoperative plan of the patient;
    removing the osteotomy guide;
    opening first and second faces of the osteotomy to form a first angle using a patient-specific spreader; and
    inserting a blade guard against a posterior bone surface of the tibia.

12. An osteotomy method comprising:
    attaching a patient-specific osteotomy guide to a corresponding surface of a tibia of a patient, the osteotomy guide having a patient-specific three-dimensional engagement surface made preoperatively to conform as a negative surface of the corresponding surface of the tibia;
    making an osteotomy at a patient-specific orientation through a resection slot of the osteotomy guide;
    removing the osteotomy guide;
    opening first and second faces of the osteotomy to form an implant insertion angle;
    securing the first and second faces of the osteotomy at the implant-insertion angle;
    implanting an osteotomy implant having a patient-specific wedge angle that is smaller than the implant-insertion angle; and
    bringing the first and second faces of the osteotomy to the patient-specific wedge angle and in contact with the osteotomy implant.

13. The osteotomy method of claim 12, further comprising attaching a fixation plate across the osteotomy.

14. The osteotomy method of claim 12, further comprising drilling a stress-relief hole along an end of the osteotomy guided by the osteotomy guide.

* * * * *

UNITED STATES PATENT AND TRADEMARK OFFICE
CERTIFICATE OF CORRECTION

PATENT NO. : 8,632,547 B2  
APPLICATION NO. : 13/106295  
DATED : January 21, 2014  
INVENTOR(S) : William Maxson et al.

Page 1 of 1

It is certified that error appears in the above-identified patent and that said Letters Patent is hereby corrected as shown below:

On the Title Page, Item (56) References Cited, Other Publications, Delete "Arthuroplasty," and insert --Arthroplasty,--.

In the Specification

Column 9, Line 45; Delete "self" and insert --shelf--.

Column 12, Line 3; Delete "(100A)" and insert --(1000A)--.

Column 12, Line 40; Delete "400, 700," and insert --1000, 1000A,--.

Column 12, Line 40; Delete "1000, 100" and insert --1000, 1000A--.

Column 12, Line 51; Delete "(100A)" and insert --(1000A)--.

Column 12, Line 54; Delete "10110," and insert --1010,--.

Column 14, Line 15; Delete "1310" and insert --1350--.

Column 14, Line 37; Delete "1000" and insert --1100--.

In the Claims

Column 16, Line 32, Claim 11; Delete "guide" and insert --guide;--.

Signed and Sealed this  
Second Day of September, 2014

Michelle K. Lee  
*Deputy Director of the United States Patent and Trademark Office*